US007704993B2

(12) United States Patent
Smith et al.

(10) Patent No.: US 7,704,993 B2
(45) Date of Patent: Apr. 27, 2010

(54) BENZAZEPINE DERIVATIVES AND METHODS OF PROPHYLAXIS OR TREATMENT OF 5HT2C RECEPTOR ASSOCIATED DISEASES

(75) Inventors: Brian Smith, San Diego, CA (US); Charles A. Gilson, III, San Diego, CA (US); Jeffrey Schultz, San Diego, CA (US); Jeffrey Smith, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 612 days.

(21) Appl. No.: 10/561,071

(22) PCT Filed: Jun. 16, 2004

(86) PCT No.: PCT/US2004/019670

§ 371 (c)(1),
(2), (4) Date: May 26, 2006

(87) PCT Pub. No.: WO2005/003096

PCT Pub. Date: Jan. 13, 2005

(65) Prior Publication Data

US 2007/0142357 A1 Jun. 21, 2007

Related U.S. Application Data

(60) Provisional application No. 60/479,280, filed on Jun. 17, 2003.

(51) Int. Cl.
*A61P 25/00* (2006.01)
*A61K 31/55* (2006.01)
*C07D 223/16* (2006.01)

(52) U.S. Cl. .................. 514/217.01; 540/594
(58) Field of Classification Search ............ 514/217.01; 540/594
See application file for complete search history.

(56) References Cited

U.S. PATENT DOCUMENTS

| | | | |
|---|---|---|---|
| 3,652,543 A | 3/1972 | Hoegerle | 540/594 |
| 3,716,639 A | 2/1973 | Hoegerle et al. | 514/217.01 |
| 3,795,683 A | 3/1974 | Brossi et al. | 540/586 |
| 4,108,989 A | 8/1978 | Holden | 514/217.01 |
| 4,111,957 A | 9/1978 | Holden et al. | 540/594 |
| 4,210,729 A | 7/1980 | Hermans et al. | 525/247 |
| 4,210,749 A | 7/1980 | Shetty | 540/594 |
| 4,233,217 A | 11/1980 | Shetty | 540/594 |
| 4,477,378 A | 10/1984 | Gold et al. | |
| 4,584,293 A | 4/1986 | Reiffen et al. | |
| 4,737,495 A | 4/1988 | Bomhard et al. | |
| 4,762,845 A | 8/1988 | Chu et al. | 514/312 |
| 4,957,914 A | 9/1990 | Clark et al. | |
| 4,988,690 A | 1/1991 | Effland et al. | 514/217.01 |
| 5,015,639 A | 5/1991 | Berger et al. | 514/210.21 |
| 5,178,786 A | 1/1993 | Jahnke et al. | 252/77 |
| 5,247,080 A | 9/1993 | Berger et al. | |
| 5,275,915 A | 1/1994 | Kojima et al. | 430/264 |
| 5,387,685 A | 2/1995 | Powell et al. | 546/143 |
| 5,412,119 A | 5/1995 | Brussee et al. | 549/419 |
| 5,422,355 A | 6/1995 | White et al. | 514/311 |
| 5,691,362 A | 11/1997 | McCormick et al. | 514/339 |
| 5,750,520 A | 5/1998 | Danilewicz et al. | 514/212 |
| 5,856,503 A | 1/1999 | Aebi et al. | 548/207 |
| 5,861,393 A | 1/1999 | Danilewicz et al. | 514/213 |
| 5,925,651 A | 7/1999 | Hutchinson | 514/307 |
| 5,939,415 A | 8/1999 | Laufer et al. | 514/224.2 |
| 5,942,535 A | 8/1999 | Laufer et al. | 514/413 |
| 5,958,943 A | 9/1999 | Laufer et al. | 514/299 |
| 6,087,346 A | 7/2000 | Glennon et al. | 514/65 |
| 6,218,385 B1 | 4/2001 | Adam et al. | 514/217.01 |
| 6,900,313 B2 | 5/2005 | Wasserscheid et al. | 544/59 |
| 6,953,787 B2 | 10/2005 | Smith et al. | 514/212.02 |
| 6,972,295 B2 | 12/2005 | Hagmann et al. | 514/345 |
| 7,105,523 B2 | 9/2006 | Stasch et al. | |
| 7,157,466 B2 | 1/2007 | McClure et al. | |
| 7,173,037 B2 | 2/2007 | Alonso-Alija et al. | |
| 7,211,591 B2 | 5/2007 | Tajima et | |
| 7,229,991 B2 | 6/2007 | Merla et al. | |
| 7,230,024 B2 | 6/2007 | Carpino et al. | |
| 7,232,823 B2 | 6/2007 | Carpino et al. | |
| 2003/0225057 A1 | 12/2003 | Smith et al. | |
| 2005/0020573 A1 | 1/2005 | Smith et al. | |
| 2007/0060568 A1 | 3/2007 | Smith et al. | |
| 2007/0275949 A1 | 11/2007 | Smith et al. | |
| 2008/0009478 A1 | 1/2008 | Smith et al. | |
| 2008/0045502 A1 | 2/2008 | Wolgast et al. | |

FOREIGN PATENT DOCUMENTS

AU  515236  3/1981

(Continued)

OTHER PUBLICATIONS

Binetti et al., Behavioral Disorders in Alzheimer Disease: A Transcultural Perspective, Arch Neurol. vol. 55, pp. 539-544, 1998.*

(Continued)

*Primary Examiner*—Brenda L Coleman
(74) *Attorney, Agent, or Firm*—Finnegan Henderson Farabow Garrett & Dunner LLP

(57) ABSTRACT

The present invention relates to certain 1-substituted-2,3,4,5-tetrahydro-3-benzazepine derivatives of Formula (I), that are modulators of the 5HT2C receptor. Accordingly, compounds of the present invention are useful for the prophylaxis or treatment of 5HT2C receptor associated diseases, conditions or disorders, such as, obesity and related disorders.

40 Claims, No Drawings

FOREIGN PATENT DOCUMENTS

| | | |
|---|---|---|
| CA | 1090797 | 12/1980 |
| CA | 2197789 | 8/1995 |
| CH | 500194 | 1/1971 |
| DE | 1944121 | 3/1970 |
| DE | 1914456 | 6/1971 |
| DE | 3315106 A1 | 11/1983 |
| DE | 3418270 | 11/1985 |
| EP | 0007070 | 1/1980 |
| EP | 0080779 A1 | 6/1983 |
| EP | 0096838 A1 | 12/1983 |
| EP | 0161350 A1 | 11/1985 |
| EP | 0174118 A2 | 3/1986 |
| EP | 0204349 | 12/1986 |
| EP | 0285287 A3 | 3/1987 |
| EP | 0285919 | 10/1988 |
| EP | 0331130 A1 | 9/1989 |
| EP | 0331130 B1 | 9/1989 |
| EP | 0285919 A1 | 10/1994 |
| EP | 0285919 B1 | 10/1994 |
| EP | 1074549 A2 | 2/2001 |
| EP | 987235 | 12/2003 |
| GB | 1196229 | 6/1970 |
| GB | 1221324 | 2/1971 |
| GB | 1225053 | 3/1971 |
| GB | 1247306 | 9/1971 |
| GB | 1268243 | 3/1972 |
| GB | 1599705 | 10/1981 |
| GB | 2133401 | 7/1984 |
| JP | 5339263 | 12/1993 |
| JP | 06298746 | 10/1994 |
| JP | 08134048 | 5/1996 |
| NL | 7807819 | 7/1978 |
| SU | 1238732 | 6/1986 |
| WO | WO 8807858 | 10/1988 |
| WO | WO 9119698 | 12/1991 |
| WO | WO 9300094 | 1/1993 |
| WO | WO9303015 | 2/1993 |
| WO | WO 9513274 | 5/1995 |
| WO | WO 9604271 | 2/1996 |
| WO | WO 9605194 | 2/1996 |
| WO | WO 9633993 | 10/1996 |
| WO | WO 97/24364 | 7/1997 |
| WO | WO 9806701 | 2/1998 |
| WO | WO 9840385 | 9/1998 |
| WO | WO 99/24411 | 5/1999 |
| WO | WO 0240471 | 5/2002 |
| WO | WO 0248124 | 6/2002 |
| WO | WO 02074746 | 9/2002 |
| WO | WO 03000663 | 1/2003 |
| WO | WO 03/027068 | 4/2003 |
| WO | WO 03/062392 | 7/2003 |
| WO | WO03062205 | 7/2003 |
| WO | WO 03/086306 | 10/2003 |
| WO | WO 2004037788 | 5/2004 |
| WO | WO2005003096 | 1/2005 |
| WO | WO2005/019179 A2 | 3/2005 |
| WO | WO 2005/019180 | 3/2005 |
| WO | WO2005/042490 A1 | 5/2005 |
| WO | WO2005/042491 A1 | 5/2005 |
| WO | WO 2005/082859 | 9/2005 |
| WO | WO 2006/013209 | 2/2006 |
| WO | WO 2006/043710 | 4/2006 |
| WO | WO2006/069363 A2 | 6/2006 |
| WO | WO2006/071740 A2 | 7/2006 |
| WO | WO2007/120517 | 10/2007 |

OTHER PUBLICATIONS

Frankle et al., Brain Serotonin Transporter Distribution in Subjects With Impulsive Aggressivity: A Positron Emission Study With [11C]McN 5652, American Journal of Psychiatry, vol. 162, pp. 915-923, 2005.*

Tohda et al., Molecular Pathopharmacology of 5-HT2C Receptors and the RNA Editing in the Brain, Journal of Pharmacological Science, vol. 100, pp. 427-432, 2006.*

Barnes, T. R., "Pharmacological Strategies for Relapse Prevention in Schizophrenia", *Psychiatry* 3(10): 37-40 (2004).

Chahal et al., IDdb Meeting Report 2000, May 17-18.

Chang et al., "Dopamine receptor binding properties of some 2, 3, 4, 5-tetrahydro-1H-3-benzazapine-7-ols with non-aromatic substituents in the 5-position", Bioorg. Med. Chem. Lett. 2:399-402 (1992).

Deady et al., "Synthesis of some tetrahydro-2-and 3-benzazepines, and of hexahydro-3-benzazocine", Journal of the Chemical Society, Perkins Transactions 1, 1973 p. 782-783.

Di Chiara G., (2002) Behavioural Brain Research, 137: 75-114.

Di Chiara et al., "Reward System and Addiction: What Dopamine Does and Doesn't Do", *Current Opinion in Pharmacology* 7:69-76 (2007).

Di Matteo et al., "Role of 5-HT$_{2C}$ Receptors in the Control of Central Dopamine Function", *Trends in Pharmacological Sciences* 22(5):229-232 (2001).

Flannery-Schroeder, E. C., "Reducing Anxiety to Prevent Depression", *Am. J. Prev. Med.* 31(6S1):S136-S142 (2006).

Fuchs et al., "Total synthesis of (+/−)-lennoxamine and (+/−)-aphanorphine by intramolecular electrophilic aromatic substitution reactions of 2-amidoacroleins", Organic Letters, 2001, pp. 3923-3925, 3(24) American Chemical Society.

Gallant et al., (1967) Current Therapy Research 9(11):579-81.

Gardent et al., "Sur quelques de l'amino-2-bromo-4 1H benzazepine-3 et de ses derives", Bull Soc. Chim. France 2:600-605 (1968).

Gerace et al., "Predictors of Weight Increases over 7 Years in Fire Fighters and Paramedics", *Preventive Medicine* 94:593-600 (1996).

Gobert et al., (2000) Synapse 36: 205-221.

Gombar et al., "Pharmacokinetics of a series of 6-chloro-2, 3, 4, 5-tetrahydro-3-substituted-1H-3-benzazepines in rats", Drug Metab. Disposition 16:367-372 (1988).

Halford et al., "Serotonergic Drugs: Effects on Appetite Expression and Use for the Treatment of Obesity", *Drugs* 67(1):27-55 (2007).

Halford, J.C.G., "Obesity Drugs in Clinical Development", *Current Opinion in Investigational Drugs* 7(4):312-318 (2006).

Hassine-Coniac et al., "Preparation et properietes d'aldehydes dans la serie de la benzazapine-3", Bull Soc. Chim. France 11:3985-3992 (1971).

Hazebroucq, "Acces a des I-H, tetrahydro-2, 3, 4, 5 benzazepines-3 one-I et a des hexahydro imidazo isoquinoleines", Ann. Chim. (1966) pp. 221-254.

Hester et al., (1968) J. Med. Chem. 11(1): 101.

Higgins et al., (2003) European Journal of Pharmacology, 480: 151.

Hitzig, P., (1994) Journal of Substance Abuse Treatment, 11(5): 489.

Im et al., (2003) Molecular Pharmacology, 64: 78-84.

Jandacek, R.J., "APD-356 (Arena)", *Current Opinion in Investigational Drugs* 6(10):1051-1056 (2005).

Jenck et al., (1998) European Neuropsychopharmacology 8: 161 (Abstract).

Jensen et al., "Potential Role of New Therapies in Modifying Cardiovascular Risk in Overweight Patients with Metabolic Risk Facts", *Obesity* 14 (Suppl. 3):143S-149S (2006).

Karasu et al., (2000) Practice Guideline for the Treatment of Patients with Major Depressive Disorder, 1-78.

Koplan et al., "Preventing Childhood Obesity: Health in the Balance, Executive Summary", http://www.nap.edu/catalog/11015.html, 41 pages (2005).

Krull, O. and Wuncsh, B., "Synthesis and Structure/NMDA Receptor Affinity Relationships of 1-Substituted Tetrahydro-3-benzazepines", *Bioorganic and Medicinal Chemistry*, 12,pp. 1439-1451, 2004.

Ladd et al., "Synthesis and dopaminergic binding of 2-aryldopamine analogues: phenethylamines, 2-benzazepines, and 9-(Aminomethyl) fluorenes", J. Med. Chem., vol. 29:1904-1912 (1986).

Lam RW, Levitt AJ (1999) (eds) Canadian Consensus Guidelines for the Treatment of Seasonal Affective Disorder, Clinical & Academic Publishing, Vancouver, BC, Canada.

Lennon et al., "Azabenzocycloheptenones Part XVIII. Amines and amino-ketones of the tetrahydro-3-benzazepine-1-one series", J. Chem. Soc. Perkin Transacts. (1975) 7:622-626.

Linda D. Williams, Chemistry Demystified 123 (2003).

Macdonald et al., "Design and synthesis of trans-3-(2-(4-((3-(3-(5-methyl-1,2,4-oxadiazolyl))-phenyl)carboxamido)cyclohexyl)ethyl)-7-methylsulfonyl-2,3,4,5-tetrahydro-1H-3-benzazepine (SB-414796): A Potent and selective dopamine D.sub.3 Receptor Antagonist", J. Med. Chem. 46:4952-4964 (2003) American Chemical Society.

Moline et al., (2001) Expert Consensus Guideline Series—Treatment of Depression in Women 2001, March: 112-113.

Müller et al., (2006) Trends in Pharmacological Sciences, 27(9): 455 (Abstract).

Navarro-Vazquez et al., "A study of aryl radical cyclization in enaminone esters", J. Org. Chem. 67:3213-20 (2002).

Niendam et al., "Neurocognitive Performance and Functional Disability in the Psychosis Prodrome", Schizophrenia Research 84:100-111 (2006).

Orioto et al., "Benzolactams—I: Alkylation of 1,2,4,5-tetrahydro-3-methyl-3h-3-benzazepin-2-one with sodium hydride and alkyl halide", Tetrahedron 36:1017-1021 (1980) Pergamon Press Ltd.

Orito et al. (Hokkaido Daigaku Kogakubu Kenkyu Hokoku (1979), (96), 41-44.

Orito et al., "Total synthesis of pseudo type of protopine alkaloids", Heterocycles 14(1) 1980.

Pauvert et al., "Silver nitrate-promoted ring enlargement of 1-tribromomethyl-1,2-dihydro-and 1-tribromomethyl-1,2,3,4-tetrahydro-isoquinoline derivatives: application to the synthesis of the anti-anginal zalebradine", Tetrahedron Letters 44:4203-4206 (2003) Pergamon Press Ltd.

Pawan et al., (1971) British Journal of Pharmacology, 41(2): 416P-417P (Caplus abstract).

Pecherer et al., "The Synthesis of Some 7- and 7,8-substituted 2,3,4,5-tetrahydro-1H-3benzazepines", J. Heterocyclic Chemistry 8(5):779-783 (1971).

Perry et al., "Prospective study of risk factors for development of non-insulin dependent diabetes in middle aged British men", BMJ (1995) 310:560-564.

Piesla et al., (2001) Schizophrenia Research 49: 95.

Porras et al., (2002) Neuropsychopharmacology 26: 311-324.

Prous Science Integrity entry 156186, 1954.

Prous Science Integrity entry 354056, 2003.

Rothman R.B., (1995) Journal of Substance Abuse Treatment, 12(6): 449.

Schlademan et al., "Synthesis of oxo- and 1-hydroxy-azobenzocycloalkanes", J. Chem. Soc. Perkin Transacts. (1972) 2:213-215.

Schaffner et al., "Preventing Severe Mental Illnesses—New Prospects and Ethical Challenges", Schizophrenia Research 51:3-15 (2001).

Smith et al., "Discovery and SAR of New Benzazepines as Potent and Selective 5-$HT_{2C}$ Receptor Agonists for the Treatment of Obesity", Bioorganic & Medicinal Chemistry Letters 15(5):1467-1470 (2005).

Smith, B. M. et al., "Discovery and Structure—Activity Relationship of (1R)-8-Chloro-2,3,4,5-tetrahydro-1-methyl-1H-3-benzazepine (Lorcaserin), a Selective Serotonin 5-$HT_{2C}$ Receptor Agonist for the Treatment of Obesity", [retrieved on Dec. 21, 2007]. Retrieved from the Internet. <URL:http://pubs.acs.org/journals/jmcmar/index.html>.

Tietz et al., "Efficient synthesis of 2, 3, 4, 5-tetrahydro-1H-3-benzazepines by intramolecular Heck reaction", Synthesis (1993) 9:876-880.

Tietze et al., "Efficient synthesis of 2,3,4,5-tetrahydro-1H-3-benzazepines by intramolecular heck reaction", Institut für Organische Chemie der Universität Göttingen, Tammannstraβe 2, D-3400 Göttingen, Germany, received Jan. 29, 1993.

Tsuang et al., "Towards the Prevention of Schizophrenia", Biol. Psychiatry 48:349-356 (2000).

Vink et al., "Risk Factors for Anxiety and Depression in the Elderly: A Review", J. Affect. Disord., doi:10.1016/j.jad.2007.06.005, 16 pages (2007).

Wise, R.A., (2000) Neuron, 26:27-33.

Wisner et al., (2002) N. Engl. J. Med., 347(3): 194-199.

Yoshinaga et al., "Prevention of Mildly Overweight Children from Development of More Overweight Condition", Preventive Medicine 38:172-174 (2004).

International Search Report dated Nov. 22, 2004 for International Application No. PCT/US04/019670.

Baindur, et al., "(±)-3-allyl-7-halo-8-hydroxy-1-phenyl-2,3,4,5-tetrahydro-1H-3-benzazepines as Selective High Affinity D1 Dopamine Receptor Antagonists: Synthesis and Structure-Activity Relationship", J. Med. Chem., 35:67-72 (1992).

Bickerdike, M. J., "5-$HT_{2C}$ Receptor Agonists as Potential Drugs for the Treatment of Obesity" Current Topics in Medicinal Chemistry, vol. 3:pp. 885-897 (2003).

Bos et al., Novel Agonists of 5$HT_{2C}$ Receptors. Synthesis and Biological Evaluation of Substituted 2-{Indol-1-yl)-1-methylethylamines and 2-(Indeno[1,2-b]pyrrol-1-yl)-1-methylethylamines. Improved Therapeutics for Obsessive Compulsive Disorder, Journal of Medicinal Chemistry (1997), 40(17), 2762-2769.

Bosch, et al., "Studies on the Synthesis of Pentacyclic Strychnos Indole Alkaloids. Photocyclization of N-chloroacetyl-1,2,3,4,5,6-hexahydro- 1,5-methanoazocino [4,3-b] Indole Derivatives", Tetrahedron, 41(12):2557-66 (1985).

Bremner, "Seven Membered Rings", Institute for Biomolecular Science, Dept. of Chemistry, University of Wollongong; "Progress in Heterocyclic Chemistry 13", Pergamon Press, Ch. 7:340-77 (2001).

Chumpradit, et al., "(±)-7-chloro-8-hydroxyl-1-(4'-[$^{125}$I]iodophenyl)-3-methyl-2,3,4,5-tetrahydro-1H-3-benzazepine: A Potential CNS D-1 Dopamine Receptor Imaging Agent", J. Med. Chem., 32:1431-5 (1989).

Clark, et al., "1,9-alkano-bridged 2,3,4,5-tetrahydro-1H-3-benzazepines with Affinity for the $\alpha_2$-Adrenoceptor and the 5-$HT_{1A}$ Receptor", J. Med. Chem., 33:633-41 (1990).

Clinical trial NCT00768612, "Study Evaluating Safety and Tolerability of Vabicaserin in Patients With Sudden Worsening of Schizophrenia Study", http://clinicaltrials.gov/ct2/show/record/NCT00768612, 2008.

DeMarinis et al., "Development of an Affinity Ligand for Purification of $\alpha_2$-Adrenoceptors from Human Platelet Membranes", J. Med. Chem., 27, 918-921 (1984).

Di Giovanni et al., "Serotonin/dopamine interaction—Focus on 5-$HT_{2C}$ receptor, a new target of psychotropic drugs" Indian Journal of Experimental Biology, vol. 40:pp. 1344-1352 (2002).

Dhonnchadha, et al., "Anxiolytic-like Effects of 5$HT_{2C}$ Ligands on Three Mouse Models of Anxiety", Behavioral Brain Research, 140:203-214 (2003).

Dixit et al., "gents Acting on Central Nervous System: Part XXIII-2-Substituted 1, 2, 3, 4, 6, 7, 12, 12a-Octahydropyrazino[2,I-b][3] benzazepines & 3-Substituted 1, 2, 3, 4, 4a, 5, 6, 11-Octahydropyrazin[I,2-b][2] benzazepines", CDRI Communication No. 1969, 893-97 (1974).

Draper, et al., "Novel Stereoselective Syntheses of the Fused Benzazepine Dopamine $D_1$ Antagonist (6aS, 13bR)-11-chloro-6, 6a,7,8,9, 13b-hexahydro-7-methyl-5H-benzo[d]naphth[2,1-b]azepin-12-ol (Sch 39166): 1. Aziridinium Salt Based Syntheses", Organic Process Research & Development, 2(3):175-85 (1998).

Draper, et al., "Novel Stereoselective Syntheses of the Fused Benzazepine Dopamine $D_1$ Antagonist (6aS, 13bR)-11-chloro-6, 6a,7,8,9, 13b-hexahydro-7-methyl-5H-benzo[d]naphth[2,1-b]azepin-12-ol (Sch 39166): 2. L-Homophenylalanine-Based Syntheses", Organic Process Research & Development, 2(3):186-93 (1998).

Garrison, "Defining obesity: An adventure in cardiovascular disease epidemiology", Journal of Nutritional Biochemistry (1998), 9(9), 493-500.

Gerritz, et al., "Two General Routes to 1,4-disubstituted-2,3,4,5-tetrahydro-1H-3-benzazepines", Organic Letters, 2(25):4099-102 (2000).

Guillory, "Generation of Polymorphs, Hydrates, Solvates, and Amorphous Solids", in *Polymorphism in Pharmaceutical Solids*, ed. Harry G. Brittain, vol. 95, chapter 5, Marcel Dekker, Inc., New York 1999, pp. 183-226.

Green and Wuts, et al., "Protective Groups in Organic Synthesis", 3$^{rd}$ Ed., Wiley and Sons (1999).

Halford, et al., "o-phenylenediacetimide and Other Compounds Related to 3,1H-benzazepine", J. Org. Chem. 17:1646-52 (1952).

Hasan, et. al., "Syntheses of N-chloroacyl-β-phenylethylamine Derivatives", Indian J. Chem., 9:1022-4 (1971).

Heys, et al., "A New Entry into C7-Oxygenated Tetrahydro-1H-3-benzazepines: Efficient Labeling with Carbon-14 in the Benzo Ring", J. Org. Chem., 54(19):4702-6 (1989).

Isaac, "The 5-HT$_{2C}$ receptor as a potential therapeutic target for the design of antiobesity and antiepileptic drugs" *Drugs of the Future* (2001), 26(4), 383-393.

Kaiser, et al., "6-(phenylthio)-substituted 2,3,4,5-tetrahydro-1H-3-benzazepines, a Novel Class of Dopamine Receptor Antagonists and Neuroleptics", J. Med. Chem., 23(9):975-6 (1980).

Klohr, et al., "An Intramolecular Photocyclization to Form the Azepino[3,4,5-cd]Indole System", Synthetic Communications 18(7):671-4 (1988).

Klein, "Outcome Success in Obesity", Obesity Research, (2001), 9(suppl. 4):354S-358S.

Küenburg, et al., "Development of a Pilot Scale Process for the Anti-Alzheimer Drug (—)-Galanthamine Using Large-Scale Phenolic Oxidative Coupling and Crystallisation-Induced Chiral Conversion", Organic Process Research & Development, 3(6):425-31 (1999).

Lacivita et al., "Selective Agents for Serotonin$_{2C}$ (5-HT$_{2C}$) Receptor" *Current Topics in Medicinal Chemistry*, vol. 6:pp. 1927-1970 (2006).

Lin, et al., "Benzindene Prostaglandins. Synthesis of Optically Pure 15-Deoxy-U-68,215 and its Enantiomer via a Modified Intramolecular Wadsworth-Emmons-Wittig Reaction", J. Org. Chem., 52(25):5594-601 (1987).

Martin et al. "5-HT$_{2C}$ receptor agonists pharmacological characteristics and therapeutic potential", *Journal of Pharmacology and Experimental Therapeutics* (1998), 286(2), 913-924.

Millan, et al., "5HT$_{2C}$ Receptors Mediate Penile Erections in Rats: Actions of Novel and Selective Agonists and Antagonists", *Eur. J. Pharmacol.* 325:9-12 (1997).

Nagle, et al., "Efficient Synthesis of β-amino Bromides", Tetrahedron Letters, 41:3011-4 (2000).

Nair, et al., "Preparation of 2,3,4,5-tetrahydro-3,1H-benzazepine-2-one", Indian J. Chem., 5:169-70 (1967).

Neumeyer, et al., "Development of a High Affinity and Stereoselective Photoaffinity Label for the D-1 Dopamine Receptor: Synthesis and Resolution of 7-[$^{125}$I]Iodo-8-hydroxy-3-methyl-1-(4'-azidophenyl)-2,3,4,5-tetrahydro-1H-3-benzazepine", J. Med. Chem., 33(2):521-6 (1990).

Okuno, et al., "Photocyclization of N-chloroacetyl-2,5-dimethoxyphenethylamine Synthesis of Pyrroloindoles", Chem. Pharm. Bull., 23(11):2584-90(1975).

Orito, et al., "Synthetic studies of heterocyclic compounds I. Alkylation and acylation of 1,2,4,5-tetrahydro-3-methyl-3H-3-benzazepin-2-one," Casreact, 1979, 93:7990 (Chemical Abstract (Online) Accession No. 1980:407990).

Pecherer, et al., "A Novel Synthesis of Aromatic Methoxy and Methylenedioxy Substituted 2,3,4,5-tetrahydro-1H-3-benzazepines", J. Het. Chem., 9:609-16 (1972).

Pfeiffer, et al., "Dopaminergic Activity of Substituted 6-chloro-1-phenyl-2,3,4,5-tetrahydro-1H-3-benzazepines", J. Med. Chem., 25(4):352-8 (1982).

"*Remington's Pharmaceutical Sciences*" 17$^{th}$ ed., Mack Publishing Company, Easton Pa.: 1418 (1985).

Rosenzweig-Lipson, et al., "Vabicaserin: effects of a novel 5HT2C agonist on medial prefrontal cortex neurotransmission, cognition and sensorimotor gating", *20th ECNP Congress*, Vienna, Austria (2007).

Tecott, et al., "Eating Disorder and Epilepsy in Mice Lacking 5-HT$_{2c}$ Serotonin Receptors", Nature, 374:542-546 (1996).

Vanderlaan, et al., "Synthesis and Oxidative Coupling of (±)-3-oxoreticuline", J. Org. Chem., 50(6):743-7 (1985).

Van Oekelen et al., "5-HT$_{2A}$ and 5-HT$_{2C}$ receptors and their atypical regulation properties" *Life Sciences*, vol. 72:pp. 2429-2449 (2003).

Weinstock, et al., "Separation of Potent Central and Renal Dopamine Agonist Activity in Substituted 6-chloro-2,3,4,5-tetrahydro-7,8-dihydroxy-1-phenyl-1H-3-benzazepines", J. Med. Chem., 23(9):973-5 (1980).

Winkler, "Obesity and hemostasis", *Archives of Gynecology and Obstetrics* (1997), 261(1), 25-29.

Wu, et al., "Amino Diol Based Asymmetric Syntheses of a Fused Benzazepine as a Selective D1 Dopamine Receptor", Organic Process Research & Development, 1(5):359-64 (1997).

Yasuda, et al., "A Novel and Stereoselective Synthesis of (±)-cephalotaxine and its Analogue", Tetrahedron Letters, 27(18):2023-6 (1986).

Yonemitsu, et al., "Photocyclization of Pharmacodynamic Amines. IV. Novel Heterocycles from N-chloroacetyl-3,4-dimethoxyphenethylamine", Journal of the American Chemical Society, 92(19):5686-90 (1970).

Yonemitsu, et al., "Photolysis of N-chloroacetyl-O-methyl-L-tyrosine to an Azaazulene", Journal of the American Chemical Society, 89(4):1039-40 (1967).

Yonemitsu, et al., "Photocyclizations of Tyrosines, Tyramines, Catecholamines, and Normescaline", Journal of the American Chemical Society, 90(3):776-84 (1968).

Yonemitsu, et al., "Photocyclization of Pharmodynamic Amines. II. X-Ray Analysis of a Noncentrosymmetric Tetracyclic Indole", Journal of the American Chemical Society, 90(23):6522-3 (1968).

International Search Report for International Application No. PCT/US03/11076 dated Oct. 16, 2003.

International Search Report for International Application No. PCT/US2004/034917 dated Feb. 2, 2005.

International Search Report for International Application No. PCT/US2004/034914 dated Mar. 15, 2005.

U.J. Griesser, "Polymorphism in the Pharmaceutical Industry", ed. Rolf Hilfiker, Wiley-VCH Verlag GmbH & Co.: pp. 211-233 (2006).

K.J. Guillory, "Polymorphism in Pharmaceutical Solids", ed. Harry G. Brittain, Marcel Dekker, Inc., vol. 95: pp. 183-226 (1999).

Abstract—Nagase et al., *Carbohydrate Research* 337(2): pp. 167-173 (2002).

* cited by examiner

BENZAZEPINE DERIVATIVES AND METHODS OF PROPHYLAXIS OR TREATMENT OF 5HT2C RECEPTOR ASSOCIATED DISEASES

CROSS REFERENCE TO RELATED APPLICATION

This application is a 35 U.S.C. §371 National Stage Application of International Application No. PCT/US2004/019670, filed Jun. 16, 2004, which claims priority to U.S. Ser. No. 60/479,280 filed Jun. 17, 2003.

FIELD OF THE INVENTION

The present invention relates to certain substituted-2,3,4,5-tetrahydro-3-benzazepine derivatives that are modulators of the $5HT_{2C}$ receptor. Accordingly, compounds of the present invention are useful for the prophylaxis or treatment of $5HT_{2C}$ receptor associated diseases, conditions or disorders, such as, obesity and related disorders.

BACKGROUND OF THE INVENTION

Obesity is a life-threatening disorder in which there is an increased risk of morbidity and mortality arising from concomitant diseases such as, but not limited to, type II diabetes, hypertension, stroke, certain forms of cancers and gallbladder disease.

Obesity has become a major healthcare issue in the Western World and increasingly in some third world countries. The increase in the number of obese people is due largely to the increasing preference for high fat content foods but also, and this can be a more important factor, the decrease in activity in most people's lives. In the last 10 years there has been a 30% increase in the incidence of obesity in the USA and that about 30% of the population of the USA is now considered obese. In spite of the growing awareness of the health concerns linked to obesity the percentage of individuals that are overweight or obese continue to increase. In fact, the percentage of children and adolescents who are defined as overweight has more than doubled since the early 1970s and about 13 perceHnt of children and adolescents are now seriously overweight. The most significant concern, from a public health perspective, is that children who are overweight grow up to be overweight or obese adults, and accordingly are at greater risk for major health problems. Therefore, it appears that the number of individuals that are overweight or obese will continue to increase.

Whether someone is classified as overweight or obese is generally determined on the basis of his or her body mass index (BMI) which is calculated by dividing their body weight (kilograms—Kg) by their height squared (meters squared—$m^2$). Thus, the units for BMI are $Kg/m^2$. The BMI is more highly correlated with body fat than any other indicator of height and weight. A person is considered overweight when they have a BMI in the range of 25-30 $kg/m^2$. Whereas a person with a BMI over 30 $kg/m^2$ is classified as obese and obesity is further divided into three classes, Class I (BMI of about 30 to about 34.9 $kg/m^2$), Class II (BMI of about 35 to 39.9 $kg/m^2$) and Class III (about 40 $kg/m^2$ or greater); see TABLE 1 below for complete classifications.

TABLE 1

CLASSIFICATION OF WEIGHT BY BODY MASS INDEX (BMI)

| BMI | CLASSIFICATION |
|---|---|
| <18.5 | Underweight |
| 18.5-24.9 | Normal |
| 25.0-29.9 | Overweight |
| 30.0-34.9 | Obesity (Class I) |
| 35.0-39.9 | Obesity (Class II) |
| >40 | Extreme Obesity (Class III) |

As the BMI increases for an individual there is an increased risk of morbidity and mortality relative to an individual with normal BMI. Accordingly, overweight and obese individuals (BMI of about 25 $kg/m^2$ and above) are at increased risk for physical ailments such as, but not limited to, high blood pressure, cardiovascular disease (particularly hypertension), high blood cholesterol, dyslipidemia, type II (non-insulin dependent) diabetes, insulin resistance, glucose intolerance, hyperinsulinemnia, coronary heart disease, angina pectoris, congestive heart failure, stroke, gallstones, cholescystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), diseases of reproduction (such as sexual dysfunction, both male and female, including male erectile dysfunction), bladder control problems (such as stress incontinence), uric acid nephrolithiasis, psychological disorders (such as depression, eating disorders, distorted body image, and low self esteem). Research has shown that even a modest reduction in body weight can correspond to a significant reduction in the risk of developing other ailments, such as, but not limited to, coronary heart disease.

As mentioned above, obesity increases the risk of developing cardiovascular diseases. Coronary insufficiency, atheromatous disease, and cardiac insufficiency are at the forefront of the cardiovascular complications induced by obesity. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for NIDDM and coronary heart disease and the potential value of an integrated approach to the prevention of these conditions based on the prevention of obesity [Perry, I. J., et al. *BMJ* 310, 560-564 (1995)]. It is estimated that if the entire population had an ideal weight, the risk of coronary insufficiency would decrease by 25% and the risk of cardiac insufficiency and of cerebral vascular accidents by 35%.

Diabetes has also been implicated in the development of kidney disease, eye diseases and nervous-system problems. Kidney disease, also called nephropathy, occurs when the kidney's "filter mechanism" is damaged and protein leaks into urine in excessive amounts and eventually the kidney fails. Diabetes is also a leading cause of damage to the retina and increases the risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

The first line of treatment for individuals that are overweight or obese is to offer diet and life style advice, such as, reducing the fat content of their diet and increasing their physical activity. However many patients find these difficult to maintain and need additional help from drug therapy to sustain results from these efforts.

Most currently marketed products have been unsuccessful as treatments for obesity owing to a lack of efficacy or unacceptable side-effect profiles. The most successful drug so far was the indirectly acting 5-hydroxytryptamine (5-HT) agonist d-fenfluramine (Redux™) but reports of cardiac valve defects in up to one third of the patient population led to its withdrawal by the FDA in 1998.

In addition, two drugs have recently been launched in the USA and Europe: Orlistat (Xenical™), a drug that prevents absorption of fat by the inhibition of pancreatic lipase, and Sibutramine (Reductil™), a 5-HT/noradrenaline re-uptake inhibitor. However, side effects associated with these products may limit their long-term utility. Treatment with Xenical™ is reported to induce gastrointestinal distress in some patients, while Sibutramine has been associated with raised blood pressure in some patients.

Serotonin (5-HT) neurotransmission plays an important role in numerous physiological processes both in health and in psychiatric disorders. 5-HT has been implicated in the regulation of feeding behavior for some time. 5-HT works by inducing a feeling of fullness or satiety so eating stops earlier and fewer calories are consumed. It has been shown that a stimulatory action of 5-HT on the $5HT_{2C}$ receptor plays an important role in the control of eating and in the anti-obesity effect of d-fenfluramine. As the $5HT_{2C}$ receptor is expressed in high density in the brain (notably in the limbic structures, extrapyramidal pathways, thalamus and hypothalamus i.e. PVN and DMH, and predominantly in the choroid plexus) and is expressed in low density or is absent in peripheral tissues, a selective $5HT_{2C}$ receptor agonist can be an effective and safe anti-obesity agent. Also, $5HT_{2C}$ knockout mice are overweight with cognitive impairment and susceptibility to seizure thus establishing the clear use for a $5HT_{2C}$ receptor agonist in $5HT_{2C}$ receptor associated diseases or disorders.

The $5HT_{2C}$ receptor plays a role in obsessive compulsive disorder, some forms of depression, and epilepsy. Accordingly, $5HT_{2C}$ receptor agonists can have anti-panic properties, and properties useful for the treatment of sexual dysfunction. In addition, $5HT_{2C}$ receptor agonists are useful for the treatment of psychiatric symptoms and behaviors in individuals with eating disorders such as, but not limited to, anorexia nervosa and bulimia nervosa. Individuals with anorexia nervosa often demonstrate social isolation. Anorexic individuals often present symptoms of being depressed, anxious, obsession, perfectionistic traits, and rigid cognitive styles as well as sexual disinterest. Other eating disorders include, anorexia nervosa, bulimia nervosa, binge eating disorder (compulsive eating) and ED-NOS (i.e., eating disorders not otherwise specified—an official diagnosis). An individual diagnosed with ED-NOS possess atypical eating disorders including situations in which the individual meets all but a few of the criteria for a particular diagnosis. What the individual is doing with regard to food and weight is neither normal nor healthy.

In addition, the $5HT_{2C}$ receptor is also involved in other diseases, conditions and disorders; such as Alzheimer Disease (AD). Therapeutic agents currently prescribed for Alzheimer's disease (AD) are cholinomimetic agents that act by inhibiting the enzyme acetylcholinesterase. The resulting effect is increased levels of acetylcholine, which modestly improves neuronal function and cognition in patients with AD. Although, dysfunction of cholinergic brain neurons is an early manifestation of AD, attempts to slow the progression of the disease with these agents have had only modest success, perhaps because the doses that can be administered are limited by peripheral cholinergic side effects, such as tremors, nausea, vomiting, and dry mouth. In addition, as AD progresses, these agents tend to lose their effectiveness due to continued cholinergic neuronal loss.

Therefore, there is a need for agents that have beneficial effects in AD, particularly in alleviating symptoms by improving cognition and slowing or inhibiting disease progression, without the side effects observed with current therapies. Therefore, serotonin $5HT_{2C}$ receptors, which are exclusively expressed in brain, are attractive targets.

A major feature of AD is the formation of senile plaques made of amyloid deposits in a selected area of the brain. New therapies should focus on prevention of the production of these senile plaques. An amyloid deposit composed mainly of beta-amyloid peptide (Aβ) occupies the plaque center. Aβ is a peptide of 40 to 43 residues derived from a larger amyloid precursor protein, APP [Selkoe D J, et al. *Ann Rev Neurosci*, 1994, 17:489-517]. APP is a ubiquitous transmembrane glycoprotein that is present at high levels in brain cells. APP also exists as secreted forms. By cleavage in the Aβ region of APP, the long N-terminal fragment (secreted APP, APPs) is secreted into the extracellular space. The rate of Aβ production appears to be inversely coupled to rate APPs secretion. In several cell cultures, APPs secretion was accompanied by reductions in secreted Aβ [Buxbaum J D, et al. *Proc Nat Acad Sci*, 1993, 90:9195-9198; Gabuzda D, et al. *J Neurochem*, 1993, 61:2326-2329; Hung A Y, et al. *J Biol Chem*, 1993, 268:22959-22962; and Wolf B A, et al. *J Biol Chem*, 1995, 270:4916-4922], suggesting that stimulated secretory processing of APP into secreted APPs is associated with reduced formation of potentially amyloidogenic derivatives, or plaques.

APPs is found in plasma and cerebrospinal fluid [Ghiso J, et al. *Biochem Biophys Res Comm*, 1989, 163:430-437; and Podlisny M B, et al. *Biochem Biophys Res Commun*, 1990, 167:1094-1101]. Considering the abundance of both membrane-bound APP and APPs, they are likely to have significant biological functions. Current knowledge about APP functions indicates APP is critically required for the maintenance of neuronal and synaptic structure and function. Membrane-bound APP has been suggested to have a receptor-like structure [Kang J, et al. *Nature*, 1987, 325:733-736], with the cytoplasmic domain capable of complexing with a GTP-binding protein [Nishimoto I., et al. *Nature*, 1993, 362:75-79]. Membrane-embedded full-length APP might also have a cell adhesion function [Qiu W., et al. *J Neurosci*, 1995, 15:2157-2167].

APPs has been shown to be neurotrophic and neuroprotective in vitro [Mattson M P, et al. *Neuron*, 1993, 10:243-254; and Qiu W., et al. *J Neurosci*, 1995, 15:2157-2167]. Other proposed functions for APPs include the regulation of blood coagulation [Cole G M, et al. *Biochem Biophys Res Commun*, 1990, 170:288-295; Smith R P, et al. *Science*, 1990, 248: 1126-1128; and Van Nostrand et al. *Science*, 1990, 248:745-748], wound-healing [Cunningham J M, et al. *Histochemistry*, 1991, 95:513-517], extracellular protease activity [Oltersdorf T, et al. *Nature* (London), 1989, 341:144-147; and Van Nostrand W E, et al. *Nature*, 1989, 341:546-548], neurite extension [Jin L., et al. *J Neurosci*, 1994, 14:5461-5470; and Robakis N K, et al. in *Molecular Biology of Alzheimer's Disease*. (T. Miyatake, D. J. Selkoe and Y. Ihara, ed.), 1990, pp. 179-188, Elsevier Science Publishers B.V., Amsterdam], cell adhesiveness [Schubert D, et al. *Neuron*, 1989, 3:689-694], cell growth, [Bhasin R., et al. *Proc Natl Acad Sci USA*, 1991, 88:10307-10311; and Saitoh T., *Cell*, 1989, 58:615-622], and differentiation [Araki W., et al. *Biochem Biophys Res Commun*, 1991, 181:265-271; Milward E A, et al. *Neuron*, 1991, 9:129-137; and Yamamoto K, et al. *J Neurobiol*, 1994, 25:585-594].

The non-selective serotonin $5HT_{2C}$ agonist dexnorfenfluramine (DEXNOR) stimulated amyloid precursor protein (APPs) secretion in guinea pigs while reducing levels of Aβ production in vivo following repeat administration [Arjona A, et al. "Effect of a $5HT_{2C}$ serotonin agonist, dexnorfenfluramine, on amyloid precursor protein metabolism in guinea pigs," *Brain Res*, 2002, 951:135-140]. Guinea pigs were chosen because guinea pig and human APP exhibit 98% sequence homology [Beck M, et al. *Biochem Biophys Acta*, 1997, 1351: 17-21], the proteins are processed similarly [Beck M., et al. *Neuroscience*, 1999, 95:243-254], and the Aβ peptide sequences are identical [Johnstone E M, et al. *Brain Res Mol Brain Res*, 1991, 10:299-305]. Although DEXNOR is non-selective, the observed effects were attenuated by a selective serotonin $5HT_{2C}$ antagonist, while a selective serotonin $HT_{2A}$ antagonist did not reverse the DEXNOR effects, indicating the serotonin $5HT_{2C}$ receptors are the most relevant target for this effect.

In addition, 5-HT stimulates APPs ectodomain secretion via the serotonin $5HT_{2A}$ and $5HT_{2C}$ receptors [Nitsch R M, et al. *J Biol Chem*, 1996, 271(8):4188-4194]. In this study, researchers stimulated 3T3 fibroblasts with serotonin (5-HT), which were stably expressing serotonin $5HT_{2A}$ or $5HT_{2C}$ receptors. 5-HT increased APPs secretion in a dose-dependent manner in both cell lines. Maximal stimulation of APPs secretion peaked at about 4-fold. Selective serotonin $5HT_{2A}$ and $5HT_{2C}$ antagonists blocked the effects in each cell line.

A serotonin $5HT_{2C}$ receptor agonist can be effective for treating AD and preventing senile plaques. Support for this claim comes from the fact that Aβ is known to be neurotoxic and a key component in senile plaques involved in AD, APPs secretion and Aβ levels seem to be inversely related, and serotonin $5HT_{2C}$ agonists increase levels of APPs in vitro in cell lines stably expressing serotonin $5HT_{2C}$ receptors while in vivo serotonin $5HT_{2C}$ agonists increase levels of APPs and decrease levels of Aβ as measured in cerebral spinal fluid of guinea pigs.

Evidence exists supporting the use of a compound of the present invention with agonist activity at the serotonin $5HT_{2C}$ receptor for the treatment of AD. The compound of the invention can be used alone or in combination with another agent or agents (such as but not limited to AChE inhibitors) that are typically prescribed for AD.

Another disease, disorder or condition that can is associated with the function of the $5HT_{2C}$ receptor is erectile dysfunction (ED). Erectile dysfunction is the inability to achieve or maintain an erection sufficiently rigid for intercourse, ejaculation, or both. An estimated 20-30 million men in the United States have this condition at some time in their lives. The prevalence of the condition increases with age. Five percent of men 40 years of age report ED. This rate increases to between 15% and 25% by the age of 65, and to 55% in men over the age of 75 years.

Erectile dysfunction can result from a number of distinct problems. These include loss of desire or libido, the inability to maintain an erection, premature ejaculation, lack of emission, and inability to achieve an orgasm. Frequently, more than one of these problems presents themselves simultaneously. The conditions may be secondary to other disease states (typically chronic conditions), the result of specific disorders of the urogenital system or endocrine system, secondary to treatment with pharmacological agents (e.g. antihypertensive drugs, antidepressant drugs, antipsychotic drugs, etc.) or the result of psychiatric problems. Erectile dysfunction, when organic, is primarily due to vascular irregularities associated with atherosclerosis, diabetes, and hypertension.

There is evidence for use of a serotonin $5HT_{2C}$ agonist for the treatment of sexual dysfunction in males and females. The serotonin $5HT_{2C}$ receptor is involved with the processing and integration of sensory information, regulation of central monoaminergic systems, and modulation of neuroendocrine responses, anxiety, feeding behavior, and cerebrospinal fluid production [Tecott, L. H., et al. *Nature* 374: 542-546 (1995)]. In addition, the serotonin $5HT_{2C}$ receptor has been implicated in the mediation of penile erections in rats, monkeys, and humans.

The exact mechanism by which $5HT_{2C}$ receptors mediate penile erections remains unknown. However, there is good evidence, indirect and direct, supporting the role of serotonin $5HT_{2C}$ receptors in the mediation of penile erections. Anatomical studies have shown that the penis receives autonomic innervation from sympathetic and parasympathetic nuclei located in the spinal cord [Pescatori E S, et al. *J Urol* 1993; 149: 627-32]. In agreement, experimental and clinical data support that penile erections are controlled by a spinal reflex. A closer analysis showed that activation of $5HT_2$ spinal receptors facilitated pudendal reflex in anesthetized cats [Danuser H and Thor K B, *Br J Pharmacol* 1996; 118: 150-4]. Accordingly, stimulation of $5HT_{2C}$ receptors has been shown to be proerectile [Millan M J, et al. *European Journal of Pharmacology* 1997; 325], and $5HT_{2C}$ receptors have been described on proerectile spinal parasympathetic neurons [Bancila M et al. *Neuroscience* 1999; 92: 1523-37].

Indirect evidence comes from the research and reports of the side effects induced by the use of selective serotonin reuptake inhibitors (SSRIs). SSRIs have demonstrated antagonist action at the serotonin $5HT_{2C}$ receptors [Jenck et al. *European Journal of Pharmacology* 231: 223-229 (1993); Lightlowler et al. *European Journal of Pharmacology* 296: 137-43 (1996); and Palvimaki, E., et al. *Psychopharmacology* 126: 234-240 (1996)]. Among the most derogatory side effects of SSRIs noted in humans is increased difficulty in attaining penile erection. Although SSRIs have a rich pharmacological profile, it is believed that the antagonist effects of SSRIs at the $5HT_{2C}$ receptors could be implicated in the inhibition of penile erections [Palvimaki, E., et al. *Psychopharmacology* 126: 234-240 (1996)].

Further evidence comes from studies with a variety compounds with known agonist activity for the serotonin $5HT_{2C}$ receptor. Pharmacologic studies with rats and rhesus monkeys provide direct evidence of the proerectile properties of agonist of the serotonin 5-$HT_{2C}$ receptor [Millan M J, et al. *European Journal of Pharmacology* 1997; 325; and Pomerantz, et al. *European Journal of Pharmacology* 243:227-34 (1993)]. These pro-erectile effects were unaffected by antagonists for the serotonin $5HT_{2A}$ and $5HT_{2B}$ receptors, respectively. Antagonists of the serotonin $5HT_{2C}$ receptors attenuated the proerectile effects of the 5-$HT_{2C}$ agonists. The inhibition action corresponded to each antagonist's affinity for the 5-$HT_{2C}$ receptors. In addition, agonists of the serotonin $5HT_{2A}$ and $5HT_{2B}$ receptors did not elicit penile erections.

In summary, the $5HT_{2C}$ receptor is a validated and well-accepted receptor target for the prophylaxis and/or treatment of $5HT_{2C}$ mediated receptor diseases and disorders, such as, obesity, eating disorders, psychiatric disorders, Alzheimer Disease, sexual dysfunction and disorders related thereto. It can be seen that there exists a need for selective $5HT_{2C}$ receptor agonists that can safely address these needs. The present invention is directed to these, as well as other, important ends.

SUMMARY OF THE INVENTION

The present invention is drawn to compounds which bind to and modulate the activity of the $5HT_{2C}$ receptor, and uses thereof. The term $5HT_{2C}$ receptor as used herein includes the human sequences found in GeneBank accession number AF498983, naturally-occurring allelic variants, mammalian orthologs, and recombinant mutants thereof.

One aspect of the present invention pertains to certain substituted-2,3,4,5-tetrahydro-3-benzazepine derivatives as represented by Formula (I):

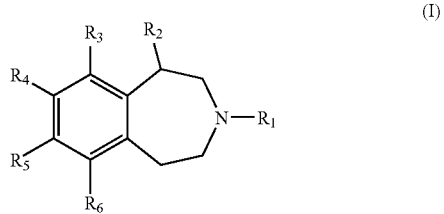

wherein:
$R_1$ is H or $C_{1-8}$ alkyl;
$R_2$ is $C_{1-4}$ alkyl, —$CH_2$—O—$C_{1-4}$ alkyl, $C_{1-4}$ haloalkyl or $CH_2OH$; and
$R_3$, $R_4$, $R_5$ and $R_6$ are each independently H, $C_{1-4}$ alkyl, amino, cyano, halogen, $C_{1-4}$ haloalkyl, nitro or OH; or
a pharmaceutically acceptable salt, hydrate and solvate thereof;
provided that when $R_2$ is $C_{1-4}$ alkyl, —$CH_2$—O—$C_{1-4}$ alkyl, and $CH_2OH$ then $R_3$ and $R_6$ are not both hydrogen.

Some embodiments of the present invention are compounds of Formula (I) wherein the compounds are the R enantiomers.

Some embodiments of the present invention are compounds of Formula (I) wherein the compounds are the S enantiomers.

Another aspect of the present invention also pertains to pharmaceutical compositions comprising one or more compounds of the invention, and one or more pharmaceutically acceptable carriers.

Another aspect of the present invention pertains to methods of modulating a $5HT_{2C}$ receptor comprising contacting said receptor with a therapeutically effective amount or dose of a compound as described herein. Preferably, compounds of the present invention are agonists of the $5HT_{2C}$ receptor.

Another aspect of the present invention pertains to methods of prophylaxis or treatment of disorders of the central nervous system; damage to the central nervous system; cardiovascular disorders; gastrointestinal disorders; diabetes insipidus or sleep apnea comprising administering to an individual in need of such prophylaxis or treatment a therapeutically effective amount or dose of a compound of the present invention or a pharmaceutical composition thereof.

Another aspect of the present invention pertains to methods of decreasing food intake of an individual comprising administering to said individual a therapeutically effective amount or dose of a compound of the present invention or a pharmaceutical composition thereof.

Another aspect of the present invention pertains to methods of inducing satiety in an individual comprising administering to said individual a therapeutically effective amount or dose of a compound of the present invention or a pharmaceutical composition thereof.

Another aspect of the present invention pertains to methods of controlling weight gain of an individual comprising administering to said individual suffering from weight control a therapeutically effective amount or dose of a compound of the present invention or a pharmaceutical composition thereof.

Another aspect of the present invention pertains to methods of producing a pharmaceutical composition comprising admixing at least one compound of the present invention and at least one pharmaceutically acceptable carrier.

Another aspect of the present invention pertains to compounds, as described herein, for use in a method of treatment of the human or animal body by therapy.

Another aspect of the present invention pertains to compounds, as described herein, for use in a method of prophylaxis or treatment of disorders of the central nervous system; damage to the central nervous system; cardiovascular disorders; gastrointestinal disorders; diabetes insipidus or sleep apnea of the human or animal body by therapy.

Another aspect of the present invention pertains to use of compounds, as described herein, for the manufacture of a medicament for use in the treatment or prophylaxis of disorders of the central nervous system; damage to the central nervous system; cardiovascular disorders; gastrointestinal disorders; diabetes insipidus or sleep apnea.

In some embodiments, the disorders of the central nervous system are selected the group consisting of depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, Alzheimer disease, age-related behavioral disorders, behavioral disorders associated with dementia, organic mental disorders, mental disorders in childhood, aggressivity, age-related memory disorders, chronic fatigue syndrome, drug and alcohol addiction, obesity, bulimia, anorexia nervosa and premenstrual tension. In further embodiments, the disorder of the central nervous system is obesity. In further embodiments, the disorder of the central nervous system is Alzheimer disease. In further embodiments, the sexual dysfunction is Male erectile dysfunction.

In some embodiments, the damage to the central nervous system is by trauma, stroke, neurodegenerative diseases, toxic CNS diseases or infective CNS diseases. In further embodiments, the damage to the central nervous system is by encephalitis or meningitis.

In some embodiments, the cardiovascular disorder is thrombosis.

In some embodiments, the gastrointestinal disorder is dysfunction of gastrointestinal motility.

In some embodiments, the invention pertains to methods for alleviation of a symptom of any of the diseases, conditions or disorders mentioned herein.

In some embodiments, the individual is a mammal.

In some embodiments, the individual is a mammal and preferably, the mammal is a human.

In further embodiments, the human has a body mass index of about 18.5 to about 45.

In further embodiments, the human has a body mass index of about 25 to about 45.

In further embodiments, the human has a body mass index of about 30 to about 45.

In further embodiments, the human has a body mass index of about 35 to about 45.

DETAILED DESCRIPTION OF THE INVENTION

Definitions

For clarity and consistency, the following definitions will be used throughout this patent document.

Agonists shall mean moieties that interact and activate the receptor, such as the $5HT_{2C}$ receptor and initiates a physiological or pharmacological response characteristic of that receptor. For example, when moieties activate the intracellular response upon binding to the receptor, or enhance GTP binding to membranes.

The term ANTAGONISTS is intended to mean moieties that competitively bind to the receptor at the same site as agonists (for example, the endogenous ligand), but which do not activate the intracellular response initiated by the active form of the receptor, and can thereby inhibit the intracellular responses by agonists or partial agonists. Antagonists do not diminish the baseline intracellular response in the absence of an agonist or partial agonist.

Chemical Group, Moiety or Radical:

As used herein, the term "alkyl" is intended to denote hydrocarbon compounds including straight chain, branched and cyclic hydrocarbons, including for example but not limited to methyl, ethyl, n-propyl, isopropyl, cyclopropyl, n-butyl, sec-butyl, tert-butyl, cyclobutyl, cyclopropylmethyl, n-pentyl, isopentyl, tert-pentyl, cyclopentyl, cyclopentylmethyl, n-hexyl, cyclohexyl, and the like. The term "$C_{1-8}$ alkyl" refers to an alkyl group containing 1 to 8 carbon atoms. Likewise, the term "$C_{1-4}$ alkyl" refers to an alkyl group containing 1 to 4 carbon atoms. Throughout this specification, it should be understood that the term alkyl is intended to encompass both non-cyclic hydrocarbon compounds and cyclic hydrocarbon compounds. In some embodiments of the compounds of the invention, alkyl groups are non-cyclic. In further embodiments, alkyl groups are cyclic, and in further embodiments, alkyl groups are both cyclic and noncyclic. Where no preference is specified, the term "alkyl" is intended to denote groups are both cyclic and non-cyclic.

The term "amino" denotes the group —$NH_2$.

The term "cyano" denotes the group —CN.

The term "$C_{1-4}$ haloalkyl" denotes an alkyl group; defined herein, wherein the alkyl is substituted with one halogen up to fully substituted and a fully substituted $C_{1-4}$ haloalkyl can therefore be represented by the formula $C_nL_{2n+1}$ wherein L is a halogen; when more than one halogen is present then they may be the same or different and selected from the group consisting of F, Cl, Br or I. Examples of $C_{1-4}$ haloalkyl groups include: fluoromethyl, difluoromethyl, trifluoromethyl, chlorodifluoromethyl, 2,2,2-trifluoroethyl, pentafluoroethyl and the like.

The term "halogen" or "halo" denotes to a fluoro, chloro, bromo or iodo group.

The term "nitro" refers to the group —$NO_2$.

Composition shall mean a material comprising at least two compounds or two components; for example, and not limitation, a Pharmaceutical Composition is a Composition.

Contact or Contacting shall mean bringing the indicated moieties together, whether in an in vitro system or an in vivo system. Thus, "contacting" a $5HT_{2C}$ receptor with a compound of the invention includes the administration of a compound of the present invention to an individual, preferably a human, having a $5HT_{2C}$ receptor, as well as, for example, introducing a compound of the invention into a sample containing a cellular or more purified preparation containing a $5HT_{2C}$ receptor.

In Need of Prophylaxis or Treatment as used herein refers to a judgment made by a caregiver (e.g. physician, nurse, nurse practitioner, etc. in the case of humans; veterinarian in the case of animals, including non-human mammals) that an individual or animal requires or will benefit from prophylaxis or treatment. This judgment is made based on a variety of factors that are in the realm of a caregiver's expertise, but that includes the knowledge that the individual or animal is ill, or will be ill, as the result of a disease, condition or disorder that is treatable by the compounds of the invention. In general, "in need of prophylaxis" refers to the judgment made by the caregiver that the individual will become ill. In this context, the compounds of the invention are used in a protective or preventive manner. However, "in need of treatment" refers to the judgment of the caregiver that the individual is already ill, therefore, the compounds of the present invention are used to alleviate, inhibit or ameliorate the disease, condition or disorder.

Individual as used herein refers to any animal, including mammals, preferably mice, rats, other rodents, rabbits, dogs, cats, swine, cattle, sheep, horses, or primates, and most preferably humans.

Pharmaceutical Composition shall mean a composition comprising at least one active ingredient, whereby the composition is amenable to investigation for a specified, efficacious outcome in a mammal (for example, and not limitation, a human). Those of ordinary skill in the art will understand and appreciate the techniques appropriate for determining whether an active ingredient has a desired efficacious outcome based upon the needs of the artisan.

Therapeutically Effective Amount as used herein refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

Compounds of the Present Invention

One aspect of the present invention pertains to certain substituted-2,3,4,5-tetrahydro-3-benzazepine derivatives as represented by Formula (I):

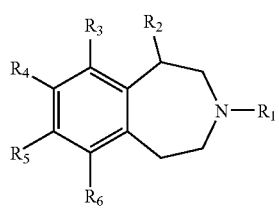

(I)

wherein:
$R_1$ is H or $C_{1-8}$ alkyl;
$R_2$ is $C_{1-4}$ alkyl, —$CH_2$—O—$C_{1-4}$ alkyl, $C_{1-4}$ haloalkyl or $CH_2OH$; and
$R_3$, $R_4$, $R_5$ and $R_6$ are each independently H, $C_{1-4}$ alkyl, amino, cyano, halogen, $C_{1-4}$ haloalkyl, nitro or OH; or a pharmaceutically acceptable salt, hydrate and solvate thereof;
provided that when $R_2$ is $C_{1-4}$ alkyl, —$CH_2$—O—$C_{1-4}$ alkyl, and $CH_2OH$ then $R_3$ and $R_6$ are not both hydrogen.

In some embodiments, when $R_1$ is H and $R_2$ is $CH_3$ then $R_3$, $R_4$ and $R_6$ can not all be hydrogens and $R_5$ can not be hydrogen or iso-propyl.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

It is understood and appreciated that compounds of Formula (I) may have one or more chiral centers, and therefore can exist as enantiomers and/or diastereomers. The invention is understood to extend to and embrace all such enantiomers, diastereomers and mixtures thereof, including but not limited to racemates. Accordingly, one embodiment of the present invention pertains to compounds of Formula (I) and formulae used throughout this disclosure that are R enantiomers. Further, one embodiment of the present invention pertains to compounds of Formula (I) and formulae used throughout this disclosure that are S enantiomers. It is understood that compounds of Formula (I) and formulae used throughout this disclosure are intended to represent all individual enantiomers and mixtures thereof, unless stated or shown otherwise.

In some embodiments of the present invention are compounds of Formula (I) wherein $R_1$ is H. In some embodiments, compounds can be represented by Formula (Ia) as illustrated below:

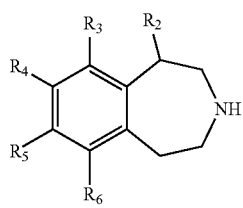

(Ia)

wherein each variable in Formula (Ia) has the same meaning as described herein, supra and infra.

Some embodiments of the present invention are compounds of Formula (I) wherein $R_1$ is $C_{1-8}$ alkyl. In some embodiments $R_1$ is methyl. In some embodiments, compounds can be represented by Formula (Ib) as illustrated below:

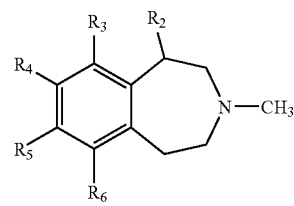

(Ib)

wherein each variable in Formula (Ib) has the same meaning as described herein, supra and infra.

In some embodiments $R_1$ is ethyl. In some embodiments $R_1$ is n-propyl. In some embodiments $R_1$ is iso-propyl. In some embodiments $R_1$ is n-butyl.

Some embodiments of the present invention are compounds of Formula (I) wherein $R_2$ is $C_{1-4}$ alkyl. In some embodiments $R_2$ is methyl. In some embodiments, compounds can be represented by Formula (Ic) as illustrated below:

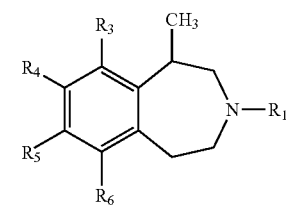

(Ic)

wherein each variable in Formula (Ic) has the same meaning as described herein, supra and infra.

In further embodiments $R_2$ is ethyl. In some embodiments $R_2$ is iso-propyl. In some embodiments $R_2$ is n-butyl.

Some embodiments of the present invention are compounds of Formula (I) wherein $R_2$ is $C_{1-4}$ haloalkyl. Examples of a $C_{1-4}$ haloalkyl group include, but are not limited to, $CH_2F$, $CHF_2$, $CF_3$, $CH_2CHF_2$, $CH_2CH_2F$, $CH_2CF_3$ and $CF_2CF_3$. In some embodiments $R_2$ is —$CF_3$.

Some embodiments of the present invention are compounds of Formula (I) wherein $R_3$ is H. In some embodiments $R_3$ is $C_{1-4}$ alkyl. In some embodiments $R_3$ is methyl (i.e., —$CH_3$).

Some embodiments of the present invention are compounds of Formula (I) wherein $R_3$ is amino.

Some embodiments of the present invention are compounds of Formula (I) wherein $R_3$ is cyano.

Some embodiments of the present invention are compounds of Formula (I) wherein $R_3$ is halogen. In some embodiments $R_3$ is a fluorine atom. In some embodiments, compounds can be represented by Formula (Ie) as illustrated below:

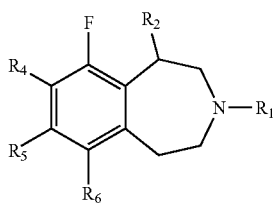

(Ie)

wherein each variable in Formula (Ie) has the same meaning as described herein, supra and infra. In some embodiments, compounds of the present invention are of Formula (Ie) and $R_2$ is $C_{1-4}$ alkyl; in further embodiments, $R_2$ is $CH_3$.

In some embodiments, $R_3$ is a chlorine atom. In some embodiments, compounds can be represented by Formula (Ig) as illustrated below:

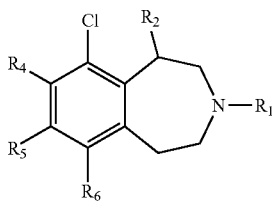

(Ig)

wherein each variable in Formula (Ig) has the same meaning as described herein, supra and infra. In some embodiments, compounds of the present invention are of Formula (Ig) and $R_2$ is $C_{1-4}$ alkyl; in further embodiments, $R_2$ is $CH_3$.

In some embodiments $R_3$ is a bromine atom.

In some embodiments $R_3$ is an iodine atom.

Some embodiments of the present invention are compounds of Formula (I) wherein $R_3$ is $C_{1-4}$ haloalkyl. In some embodiments $R_3$ is $CF_3$.

Some embodiments of the present invention are compounds of Formula (I) wherein $R_3$ is nitro.

Some embodiments of the present invention are compounds of Formula (I) wherein $R_3$ is —OH.

Some embodiments of the present invention are compounds of Formula (I) wherein $R_4$ is H.

Some embodiments of the present invention are compounds of Formula (I) wherein $R_4$ is $C_{1-4}$ alkyl. In some embodiments, $R_4$ is methyl (i.e., —$CH_3$).

Some embodiments of the present invention are compounds of Formula (I) wherein $R_4$ is amino.

Some embodiments of the present invention are compounds of Formula (I) wherein $R_4$ is cyano.

Some embodiments of the present invention are compounds of Formula (I) wherein $R_4$ is halogen. In some embodiments $R_4$ is a fluorine atom. In some embodiments, compounds can be represented by Formula (Ii) as illustrated below:

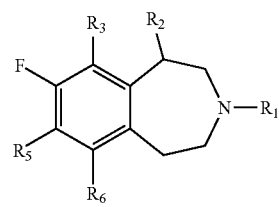

(Ii)

wherein each variable in Formula (Ii) has the same meaning as described herein, supra and infra. In some embodiments, compounds of the present invention are of Formula (Ii) and $R_2$ is $C_{1-4}$ alkyl; in further embodiments, $R_2$ is $CH_3$.

In some embodiments $R_4$ is a chlorine atom. In some embodiments, compounds can be represented by Formula (Ik) as illustrated below:

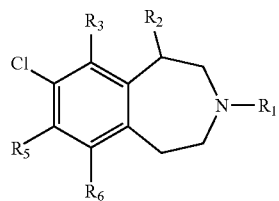

(Ik)

wherein each variable in Formula (Ik) has the same meaning as described herein, supra and infra. In some embodiments, some embodiments of the present are of Formula (Ik) and $R_2$ is $C_{1-4}$ alkyl; in further embodiments, $R_2$ is $CH_3$.

In some embodiments $R_4$ is a bromine atom.

In some embodiments $R_4$ is an iodine atom.

Some embodiments of the present invention are compounds of Formula (I) wherein $R_4$ is $C_{1-4}$ haloalkyl. In some embodiments $R_4$ is $CF_3$.

Some embodiments of the present invention are compounds of Formula (I) wherein $R_4$ is nitro.

Some embodiments of the present invention are compounds of Formula (I) wherein $R_4$ is —OH.

Some embodiments of the present invention are compounds of Formula (I) wherein $R_5$ is H.

Some embodiments of the present invention are compounds of Formula (I) wherein $R_5$ is $C_{1-4}$ alkyl. In some embodiments $R_5$ is methyl (i.e., —$CH_3$).

Some embodiments of the present invention are compounds of Formula (I) wherein $R_5$ is amino.

Some embodiments of the present invention are compounds of Formula (I) wherein $R_5$ is cyano.

Some embodiments of the present invention are compounds of Formula (I) wherein $R_5$ is halogen. In some embodiments $R_5$ is a fluorine atom. In some embodiments, compounds can be represented by Formula (Im) as illustrated below:

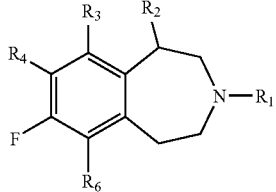

(Im)

wherein each variable in Formula (Im) has the same meaning as described herein, supra and infra. In some embodiments, compounds of the present invention are of Formula (Im) and $R_2$ is $C_{1-4}$ alkyl; in further embodiments, $R_2$ is $CH_3$.

Some embodiments of the present invention are compounds of Formula (I) wherein $R_5$ is halogen. In some embodiments $R_5$ is a chlorine atom. In some embodiments, compounds can be represented by Formula (Io) as illustrated below:

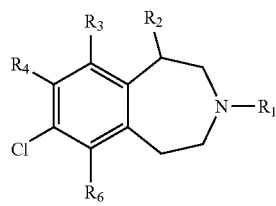

(Io)

wherein each variable in Formula (Io) has the same meaning as described herein, supra and infra. In some embodiments, compounds of the present invention are of Formula (Io) and $R_2$ is $C_{1-4}$ alkyl; in further embodiments $R_2$ is $CH_3$.

In some embodiments $R_5$ is a bromine atom. In some embodiments $R_5$ is an iodine atom.

Some embodiments of the present invention are compounds of Formula (I) wherein $R_5$ is $C_{1-4}$ haloalkyl. In some embodiments $R_5$ is $CF_3$.

Some embodiments of the present invention are compounds of Formula (I) wherein $R_5$ is nitro.

Some embodiments of the present invention are compounds of Formula (I) wherein $R_5$ is —OH Some embodiments of the present invention are compounds of Formula (I) wherein $R_6$ is H.

Some embodiments of the present invention are compounds of Formula (I) wherein $R_6$ is $C_{1-4}$ alkyl. In some embodiments $R_6$ is —$CH_3$.

Some embodiments of the present invention are compounds of Formula (I) wherein $R_6$ is amino.

Some embodiments of the present invention are compounds of Formula (I) wherein $R_6$ is cyano.

Some embodiments of the present invention are compounds of Formula (I) wherein $R_6$ is halogen. In some embodiments $R_6$ is a fluorine atom. In some embodiments, compounds can be represented by Formula (Iq) as illustrated below:

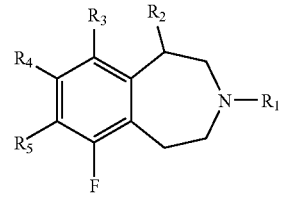

(Iq)

wherein each variable in Formula (Iq) has the same meaning as described herein, supra and infra. In some embodiments, compounds of the present invention are of Formula (Iq) and $R_2$ is $C_{1-4}$ alkyl; in further embodiments $R_2$ is $CH_3$.

In some embodiments $R_6$ is a chlorine atom. In some embodiments, compounds can be represented by Formula (Is) as illustrated below:

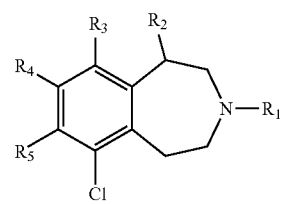

(Is)

wherein each variable in Formula (Is) has the same meaning as described herein, supra and infra. In some embodiments, compounds of the present invention are of Formula (Is) and $R_2$ is $C_{1-4}$ alkyl in further embodiments, $R_2$ is $CH_3$.

In some embodiments $R_6$ is a bromine atom. In some embodiments $R_6$ is an iodine atom.

Some embodiments of the present invention are compounds of Formula (I) wherein $R_6$ is $C_{1-4}$ haloalkyl. In some embodiments $R_6$ is $CF_3$.

Some embodiments of the present invention are compounds of Formula (I) wherein $R_6$ is nitro.

Some embodiments of the present invention are compounds of Formula (I) wherein $R_6$ is —OH.

In some embodiments, compounds of the present invention are of Formula (Ic) wherein $R_1$ is H or $C_{1-8}$ alkyl, and $R_3$, $R_4$, $R_5$, and $R_6$ are each independently H or halogen.

In some embodiments, compounds of the present invention are of Formula (Ic) wherein $R_1$ is H or $CH_3$, and $R_3$, $R_4$, $R_5$, and $R_6$ are each independently H, F, Cl, or Br.

In some embodiments, compounds of the present invention are of Formula (Ic) wherein $R_1$ is H, and $R_3$ is H, F, Cl, or Br; $R_4$ is H or Cl; $R_5$ is H; and $R_6$ is H or Cl.

In some embodiments, compounds of the present invention are of Formula (Ic) wherein $R_1$ is $CH_3$, and $R_3$ is H, F, Cl, or Br; $R_4$ is H or Cl; $R_5$ is H; and $R_6$ is H or Cl.

This application is related to US Provisional Patent Application, Ser. No. 60/479,280, which is incorporated by reference in its entirety.

Still further embodiments of the present invention are compounds of Formula (I) as shown in TABLE 2 below or a pharmaceutically acceptable salt, hydrate and solvate thereof:

TABLE 2

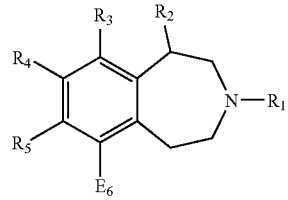

| R₁ | R₂ | R₃ | R₄ | R₅ | R₆ |
|---|---|---|---|---|---|
| H | CH₃ | Cl | H | H | Cl |
| H | CH₃ | Cl | H | Cl | H |
| H | CH₃ | Cl | Cl | H | H |
| H | CH₃ | Cl | H | H | H |
| H | CH₃ | H | H | Cl | Cl |
| H | CH₃ | H | Cl | H | Cl |
| H | CH₃ | Cl | H | H | Cl |
| H | CH₃ | H | H | H | Cl |
| H | CH₃ | F | H | H | Cl |
| H | CH₃ | F | H | Cl | H |
| H | CH₃ | F | Cl | H | H |
| H | CH₃ | F | H | H | H |
| H | CH₃ | H | H | Cl | F |
| H | CH₃ | H | Cl | H | F |
| H | CH₃ | Cl | H | H | F |
| H | CH₃ | H | H | H | F |
| H | CH₃ | Br | Cl | H | H |
| CH₃ | CH₃ | Cl | H | H | Cl |
| CH₃ | CH₃ | Cl | H | Cl | H |
| CH₃ | CH₃ | Cl | Cl | H | H |
| CH₃ | CH₃ | Cl | H | H | H |
| CH₃ | CH₃ | H | H | Cl | Cl |
| CH₃ | CH₃ | H | CL | H | Cl |
| CH₃ | CH₃ | Cl | H | H | Cl |
| CH₃ | CH₃ | H | H | H | Cl |
| CH₃ | CH₃ | F | H | H | Cl |
| CH₃ | CH₃ | F | H | Cl | H |
| CH₃ | CH₃ | F | Cl | H | H |
| CH₃ | CH₃ | F | H | H | H |
| CH₃ | CH₃ | H | H | Cl | F |
| CH₃ | CH₃ | H | Cl | H | F |
| CH₃ | CH₃ | Cl | H | H | F |
| CH₃ | CH₃ | H | H | H | F |
| CH₃ | CH₃ | Cl | H | H | Cl |
| CH₃ | CH₃ | Cl | H | Cl | H |
| CH₃ | CH₃ | Br | Cl | H | H |

Some embodiments of the present invention are compounds of Formula (I) selected from the group consisting of: 6,8-Dichloro-1-methyl-2,3,4,5-tetrahydro-1H-3-benzazepine; 6-Chloro-1-methyl-2,3,4,5-tetrahydro-1H-3-benzazepine; 8-Chloro-9-fluoro-1-methyl-2,3,4,5-tetrahydro-1H-3-benzazepine; and 8,9-Dichloro-1-methyl-2,3,4,5-tetrahydro-1H-3-benzazepine; or a pharmaceutically acceptable salt, hydrate and solvate thereof.

Some embodiments of the present invention are compounds of Formula (I) selected from the group consisting of: 6,8-Dichloro-1-methyl-2,3,4,5-tetrahydro-1H-3-benzazepine; 6-Chloro-1-methyl-2,3,4,5-tetrahydro-1H-3-benzazepine; 8-Chloro-9-fluoro-1-methyl-2,3,4,5-tetrahydro-1H-3-benzazepine; 8,9-Dichloro-1-methyl-2,3,4,5-tetrahydro-1H-3-benzazepine; and 9-bromo-8-chloro-1-methyl-2,3,4,5-tetrahydro-1H-3-benzazepine; or a pharmaceutically acceptable salt, hydrate and solvate thereof.

Some embodiments of the present invention are compounds of Formula (I) selected from the group consisting of: N-methyl-6,8-Dichloro-1-methyl-2,3,4,5-tetrahydro-1H-3-benzazepine; N-methyl-6-Chloro-1-methyl-2,3,4,5-tetrahydro-1H-3-benzazepine; N-methyl-8-Chloro-9-fluoro-1-methyl-2,3,4,5-tetrahydro-1H-3-benzazepine; N-methyl-8,9-Dichloro-1-methyl-2,3,4,5-tetrahydro-1H-3-benzazepine; and N-methyl-9-bromo-8-chloro-1-methyl-2,3,4,5-tetrahydro-1H-3-benzazepine; or a pharmaceutically acceptable salt, hydrate and solvate thereof.

Some embodiments of the present invention are compounds of Formula (I) selected from the group consisting of: (R)-6,8-Dichloro-1-methyl-2,3,4,5-tetrahydro-1H-3-benzazepine; (R)-6-Chloro-1-methyl-2,3,4,5-tetrahydro-1H-3-benzazepine; (R)-8-Chloro-9-fluoro-1-methyl-2,3,4,5-tetrahydro-1H-3-benzazepine; (R)-8,9-Dichloro-1-methyl-2,3,4,5-tetrahydro-1H-3-benzazepine; and (R)-9-bromo-8-chloro-1-methyl-2,3,4,5-tetrahydro-1H-3-benzazepine; or a pharmaceutically acceptable salt, hydrate and solvate thereof.

Some embodiments of the present invention are compounds of Formula (I) selected from the group consisting of: (S)-6,8-Dichloro-1-methyl-2,3,4,5-tetrahydro-1H-3-benzazepine; (S)-6-Chloro-1-methyl-2,3,4,5-tetrahydro-1H-3-benzazepine; (S)-8-Chloro-9-fluoro-1-methyl-2,3,4,5-tetrahydro-1H-3-benzazepine; (S)-8,9-Dichloro-1-methyl-2,3,4,5-tetrahydro-1H-3-benzazepine; and (S)-9-bromo-8-chloro-1-methyl-2,3,4,5-tetrahydro-1H-3-benzazepine; or a pharmaceutically acceptable salt, hydrate and solvate thereof.

Some embodiments of the present invention are compounds of Formula (I) selected from the group consisting of: (R)-N-methyl-6,8-Dichloro-1-methyl-2,3,4,5-tetrahydro-1H-3-benzazepine; (R)-N-methyl-6-Chloro-1-methyl-2,3,4,5-tetrahydro-1H-3-benzazepine; (R)-N-methyl-8-Chloro-9-fluoro-1-methyl-2,3,4,5-tetrahydro-1H-3-benzazepine; (R)-N-methyl-8,9-Dichloro-1-methyl-2,3,4,5-tetrahydro-1H-3-benzazepine; and (R)-N-methyl-9-bromo-8-chloro-1-methyl-2,3,4,5-tetrahydro-1H-3-benzazepine; or a pharmaceutically acceptable salt, hydrate and solvate thereof.

Some embodiments of the present invention are compounds of Formula (I) selected from the group consisting of: (S)-N-methyl-6,8-Dichloro-1-methyl-2,3,4,5-tetrahydro-1H-3-benzazepine; (S)-N-methyl-6-Chloro-1-methyl-2,3,4,5-tetrahydro-1H-3-benzazepine; (S)-N-methyl-8-Chloro-9-fluoro-1-methyl-2,3,4,5-tetrahydro-1H-3-benzazepine; (S)-N-methyl-8,9-Dichloro-1-methyl-2,3,4,5-tetrahydro-1H-3-benzazepine; and (S)-N-methyl-9-bromo-8-chloro-1-methyl-2,3,4,5-tetrahydro-1H-3-benzazepine; or a pharmaceutically acceptable salt, hydrate and solvate thereof.

At various places in the present specification substituents of compounds of the invention are disclosed in groups or in ranges. It is specifically intended that the invention include each and every individual subcombination of the members of such groups and ranges. For example, the term "$C_{1-4}$ alkyl" is specifically intended to individually and separately disclose methyl, ethyl, $C_3$ alkyl and $C_4$ alkyl.

Methods and Use

One aspect of the present invention pertains to methods of modulating a $5HT_{2C}$ receptor comprising contacting said receptor with a therapeutically effective amount or dose of a compound as described herein. Preferably, compounds of the present invention are agonists of the $5HT_{2C}$ receptor.

Another aspect of the present invention pertains to methods of prophylaxis or treatment of a $5HT_{2C}$ receptor associated disease in an individual comprising administering to the individual in need of such prophylaxis or treatment a therapeutically effective amount or dose of a compound of the present invention or a pharmaceutical composition thereof. In some embodiments, the $5HT_{2C}$ receptor associated disease is selected from the group consisting of disorders of the central nervous system; damage to the central nervous system; cardiovascular disorders; gastrointestinal disorders; diabetes insipidus and sleep apnea. In some embodiments, the individual is a mammal. Preferably, the mammal is a human.

In some embodiments, the $5HT_{2C}$ receptor associated related disease is selected from the group consisting of depression, atypical depression, bipolar disorders, anxiety, anxiety disorders, obsessive-compulsive disorders, social phobias, panic states, attention deficit hyperactivity disorder, disruptive behavior disorders, impulse control disorders, borderline personality disorder, sleep disorders (e.g., sleep apnea), autism, seizure disorders, mutism, selective mutism, childhood anxiety disorders, sexual dysfunction in males (e.g., premature ejaculation and erectile difficulty or dysfunction), sexual dysfunction in females, psychoses, schizophrenia, migraine and other conditions associated with cephalic pain or other pain, raised intracranial pressure, epilepsy, personality disorders, Alzheimer disease, age-related behavioral disorders, behavioral disorders associated with dementia, dementia of aging, organic mental disorders, mental disorders in childhood, aggressivity, age-related memory disorders, memory loss, chronic fatigue syndrome, drug and alcohol addiction, alcoholism, tobacco abuse, weight loss, obesity, bulimia, bulimia nervosa, anorexia nervosa, binge eating disorder, premenstrual tension, premenstrual syndrome (PMS or late luteal phase dysphoric disorder), post-traumatic syndrome, spinal cord injury, damage of the central nervous system (e.g., trauma, stroke, neurodegenerative diseases or toxic or infective disorders (e.g., thrombosis), gastrointestinal disorders (e.g., dysfunction of gastrointestinal motility), diabetes insipidus, and type II diabetes.

In some embodiments, the $5HT_{2C}$ receptor associated disease is selected from the group consisting of high blood pressure, hypertension, high blood cholesterol, dyslipidemia, type II (non-insulin dependent) diabetes, insulin resistance, glucose intolerance, hyperinsulinemia, coronary heart disease, angina pectoris, congestive heart failure, stroke, gallstones, cholescystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), bladder control problems (such as stress incontinence), uric acid nephrolithiasis, psychological disorders (such as depression, eating disorders, distorted body image, and low self esteem).

In some embodiments, the $5HT_{2C}$ receptor associated disease is selected from the group consisting of psychiatric symptoms and behaviors in individuals with eating disorders such as, but not limited to, anorexia nervosa and bulimia nervosa. Individuals with eating disorders often demonstrate social isolation. For example, anorexic individuals often present symptoms of being depressed, anxious, obsession, perfectionistic traits, and rigid cognitive styles as well as sexual disinterest. In addition to anorexia nervosa and bulimia nervosa, other eating disorders include, binge eating disorder (compulsive eating) and ED-NOS (i.e., eating disorders not otherwise specified—an official diagnosis). An individual diagnosed with ED-NOS possess atypical eating disorders including situations in which the individual meets all but a few of the criteria for a particular diagnosis. In essence, what the individual is doing with regard to food and weight is neither normal nor healthy.

In some embodiments, the $5HT_{2C}$ receptor associated disease is selected from the group consisting of anorexia athletica (compulsive exercising), body dysmorphic disorder (bigorexia), infection-triggered auto immune subtype of anorexia in children, orthorexia nervosa, night-eating syndrome, nocturnal sleep-related eating disorder, rumination syndrome, gourmand syndrome, Prader-Willi syndrome, pica, and cyclic vomiting syndrome.

Another aspect of the present invention pertains to methods of decreasing food intake of an individual comprising administering to the individual a therapeutically effective amount or dose of a compound of the present invention or a pharmaceutical composition thereof. In some embodiments, the individual is a mammal. Preferably, the mammal is a human. In further embodiments, the human has a body mass index of about 18.5 to about 45. In further embodiments, the human has a body mass index of about 25 to about 45. In further embodiments, the human has a body mass index of about 30 to about 45. In further embodiments, the human has a body mass index of about 35 to about 45.

Another aspect of the present invention pertains to methods of inducing satiety in an individual comprising administering to said individual a therapeutically effective amount or dose of a compound of the present invention or a pharmaceutical composition thereof. In some embodiments, the individual is a mammal. Preferably, the mammal is a human. In further embodiments, the human has a body mass index of about 18.5 to about 45. In further embodiments, the human has a body mass index of about 25 to about 45. In further embodiments, the human has a body mass index of about 30 to about 45. In further embodiments, the human has a body mass index of about 35 to about 45.

Another aspect of the present invention pertains to methods of controlling weight gain of an individual comprising administering to said individual suffering from weight control a therapeutically effective amount or dose of a compound of the present invention or a pharmaceutical composition thereof. In some embodiments, the individual is a mammal. Preferably, the mammal is a human. In further embodiments, the human has a body mass index of about 18.5 to about 45. In further embodiments, the human has a body mass index of about 25 to about 45. In further embodiments, the human has a body mass index of about 30 to about 45. In further embodiments, the human has a body mass index of about 35 to about 45.

Another aspect of the present invention pertains to methods of producing a pharmaceutical composition comprising admixing at least one compound of the present invention and at least one pharmaceutically acceptable carrier.

Another aspect of the present invention pertains to compounds, as described herein, for use in a method of prophylaxis or treatment of disorders of the central nervous system; damage to the central nervous system; cardiovascular disorders; gastrointestinal disorders; diabetes insipidus or sleep apnea of the human or animal body by therapy.

Another aspect of the present invention pertains to use of compounds, as described herein, for the manufacture of a medicament for use in the treatment or prophylaxis of disorders of the central nervous system; damage to the central nervous system; cardiovascular disorders; gastrointestinal disorders; diabetes insipidus or sleep apnea.

In some embodiments, the disorders of the central nervous system are selected the group consisting of depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, Alzheimer disease, age-related behavioral disorders, behavioral disorders associated with dementia, organic mental disorders, mental disorders in childhood, aggressivity, age-related memory disorders, chronic fatigue syndrome, drug and alcohol addiction, obesity, bulimia, anorexia nervosa and premenstrual tension. In further embodiments, the disorder of the central nervous system is obesity. In further embodiments, the disorder of the central nervous system is Alzheimer disease. In further embodiments, the sexual dysfunction is Male erectile dysfunction.

In some embodiments, the damage to the central nervous system is by trauma, stroke, neurodegenerative diseases, toxic CNS diseases or infective CNS diseases. In further embodiments, the damage to the central nervous system is by encephalitis or meningitis.

In some embodiments, the cardiovascular disorder is thrombosis.

In some embodiments, the gastrointestinal disorder is dysfunction of gastrointestinal motility.

Another aspect of the present invention pertains to methods of producing a pharmaceutical composition comprising admixing at least one compound of the present invention and at least one pharmaceutically acceptable carrier.

Another aspect of the present invention pertains to compounds, as described herein, for use in a method of treatment of the human or animal body by therapy.

Another aspect of the present invention pertains to compounds, as described herein, for use in a method of prophylaxis or treatment of disorders of the central nervous system; damage to the central nervous system; cardiovascular disorders; gastrointestinal disorders; diabetes insipidus or sleep apnea of the human or animal body by therapy.

Another aspect of the present invention pertains to use of compounds, as described herein, for the manufacture of a medicament for use in the treatment or prophylaxis of disorders of the central nervous system; damage to the central nervous system; cardiovascular disorders; gastrointestinal disorders; diabetes insipidus or sleep apnea.

Another aspect of the present invention pertains to the use of a compound of the present invention with agonist activity at the serotonin $5HT_{2C}$ receptor for the treatment and/or prophylaxis of AD and AD related disorders. The compounds of the present invention can be used alone or in combination with another agent or agents (such as but not limited to AChE inhibitors) that are typically prescribed for AD.

Combination Therapy—Prophylaxis and Treatment

In the context of the present invention, a compound of Formula (I) or pharmaceutical composition thereof can be utilized for modulating the activity of the $5HT_{2C}$ receptor associated diseases, conditions and/or disorders as described herein. Examples of modulating the activity of $5HT_{2C}$ receptor associated diseases include the prophylaxis or treatment of obesity and/or overweight by decreasing food intake, inducing satiation (i.e., the feeling of fullness), controlling weight gain, decreasing body weight and/or affecting metabolism such that the recipient loses weight and/or maintains weight. Such compounds and pharmaceutical compositions can therefore be used in the context of disorders and/or diseases where weight gain is a component of a disease and/or disorder such as those listed herein. Furthermore, compounds and composition of the present invention can be used for the prophylaxis and/or treatment of Alzheimer Disease, erectile dysfunction and other $5HT_{2C}$ receptor associated diseases and/or disorders described herein.

While the compounds of the invention can be administered as the sole active pharmaceutical agent (i.e., mono-therapy), they can also be used in combination with other pharmaceutical agents (i.e., combination-therapy) for the treatment of the diseases/conditions/disorders described herein. Therefore, another aspect of the present invention includes methods of prophylaxis and/or treatment comprising administering to an individual in need of prophylaxis and/or treatment a therapeutically effective amount of a compound of the present invention, for example Formula (I), in combination with one or more additional pharmaceutical agent as described herein.

Suitable pharmaceutical agents that can be used in combination with the compounds of the present invention include anti-obesity agents such as apolipoprotein-B secretion/microsomal triglyceride transfer protein (apo-B/MTP) inhibitors, MCR4 agonists, cholescystokinin-A (CCK-A) agonists, serotonin and norepinephrine reuptake inhibitors (for example, sibutramine), sympathomimetic agensts, $\beta_3$ adrenergic receptor agonists, dopamine agonists (for example, bromocriptine), melanocyte-stimulating hormone receptor analogs, cannabinoid 1 receptor antagonists [for example, SR141716: N-(piperidin-1-yl)-5-(4-chlorophenyl)-1-(2,4-dichlorophenyl)-4-methyl-1H-pyrazole-3-carboxamide], melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™ available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or reverse agonists, neuromedin U receptor agonists, noradrenergic anorectic agents (for example, phentermine, mazindol and the like) and appetite suppressants (for example, bupropion).

Other anti-obesity agents, including the agents set forth infra, are well known, or will be readily apparent in light of the instant disclosure, to one of ordinary skill in the art.

In some embodiments, the anti-obesity agents are selected from the group consisting of orlistat, sibutramine, bromocriptine, ephedrine, leptin, and pseudoephedrine. In a further embodiment, compounds of the present invention and combination therapies are administered in conjunction with exercise and/or a sensible diet.

It will be understood that the scope of combination-therapy of the compounds of the present invention with other anti-obesity agents, anorectic agents, appetite suppressant and related agents is not limited to those listed above, but includes in principle any combination with any pharmaceutical agent or pharmaceutical composition useful for the treatment of overweight and obese individuals.

Other suitable pharmaceutical agents, in addition to anti-obesity agents, that can be used in combination with the compounds of the present invention include agents useful in the treatment of concomitant diseases. For example, individuals that are over weight or obese increase their risk of morbidity and mortality arising from concomitant diseases, such as, but not limited to, congestive heart failure, type II diabetes, atherosclerosis, dyslipidemia, hyperinsulinemia, hypertension, insulin resistance, hyperglycemia, retinopathy, nephropathy and neuropathy. Treatment for one or more of the diseases cited herein include the use of one or more pharmaceutical agents known in the art belonging to the classes of drugs referred to, but not limited to, the following: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin II receptor antagonists and adiponectin. In accordance to one aspect of the present invention, a compound of the present can be used in combination with a pharmaceutical agent or agents belonging to one or more of the classes of drugs cited herein.

It will be understood that the scope of combination-therapy of the compounds of the present invention with other pharmaceutical agents is not limited to those listed herein, supra or infra, but includes in principle any combination with any pharmaceutical agent or pharmaceutical composition useful for the treatment diseases, conditions or disorders that are linked to overweight and obese individuals.

Some embodiments of the present invention include methods of prophylaxis or treatment of a disease, disorder or condition as described herein comprising administering to an individual in need of such prophylaxis or treatment a therapeutically effect amount or dose of a compound of the present invention in combination with at least one pharmaceutical agent selected from the group consisting of: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin II receptor antagonists and adiponectin. In some embodiments, methods of the present invention include compounds of the present invention and the pharmaceutical agents are administered separately. In further embodiments, compounds of the present invention and the pharmaceutical agents are administered together.

Suitable pharmaceutical agents that can be used in conjunction with compounds of the present invention include α-glucosidase inhibitors. α-Glucosidase inhibitors belong to the class of drugs which competitively inhibit digestive enzymes such as α-amylase, maltase, α-dextrinase, sucrase, etc. in the pancreas and or small intestine. The reversible inhibition by α-glucosidase inhibitors retard, diminish or otherwise reduce blood glucose levels by delaying the digestion of starch and sugars. Some representative examples of α-glucosidase inhibitors include acarbose, N-(1,3-dihydroxy-2-propyl)valiolamine (generic name; voglibose), miglitol, and α-glucosidase inhibitors known in the art.

Suitable pharmaceutical agents that can be used in conjunction with compounds of the present invention include sulfonylureas. The sulfonylureas (SU) are drugs which promote secretion of insulin from pancreatic β cells by transmitting signals of insulin secretion via SU receptors in the cell membranes. Examples of the sulfonylureas include glyburide, glipizide, glimepiride and other sulfonylureas known in the art.

Suitable pharmaceutical agents that can be used in conjunction with compounds of the present invention include the meglitinides. The meglitinides are benzoic acid derivatives represent a novel class of insulin secretagogues. These agents target postprandial hyperglycemia and show comparable efficacy to sulfonylureas in reducing $HbA_{1c}$. Examples of meglitinides include repaglinide, nateglinide and other meglitinides known in the art.

Suitable pharmaceutical agents that can be used in conjunction with compounds of the present invention include the biguanides. The biguanides represent a class of drugs that stimulate anaerobic glycolysis, increase the sensitivity to insulin in the peripheral tissues, inhibit glucose absorption from the intestine, suppress of hepatic gluconeogenesis, and inhibit fatty acid oxidation. Examples of biguanides include phenformin, metformin, buformin, and biguanides known in the art.

Suitable pharmaceutical agents that can be used in conjunction with compounds of the present invention include the α-glucosidase inhibitors. The α-glucosidase inhibitors competitively inhibit digestive enzymes such as α-amylase, maltase, α-dextrinase, sucrase, etc. in the pancreas and or small intestine. The reversible inhibition by α-glucosidase inhibitors retard, diminish or otherwise reduce blood glucose levels by delaying the digestion of starch and sugars. Examples of α-glucosidase inhibitors include acarbose, N-(1,3-dihydroxy-2-propyl)valiolamine (generic name; voglibose), miglitol, and α-glucosidase inhibitors known in the art.

Suitable pharmaceutical agents that can be used in conjunction with compounds of the present invention include the peroxisome proliferators-activated receptor-γ (i.e., PPAR-γ) agonists. The peroxisome proliferators-activated receptor-γ agonists represent a class of compounds that activates the nuclear receptor PPAR-γ and therefore regulate the transcription of insulin-responsive genes involved in the control of glucose production, transport and utilization. Agents in the class also facilitate the regulation of fatty acid metabolism. Examples of PPAR-γ agonists include rosiglitazone, pioglitazone, tesaglitazar, netoglitazone, GW-409544, GW-501516 and PPAR-γ agonists known in the art.

Suitable pharmaceutical agents that can be used in conjunction with compounds of the present invention include the HMG-CoA reductase inhibitors. The HMG-CoA reductase inhibitors are agents also referred to as Statin compounds that belong to a class of drugs that lower blood cholesterol levels by inhibiting hydroxymethylglutalyl CoA (HMG-CoA) reductase. HMG-CoA reductase is the rate-limiting enzyme in cholesterol biosynthesis. The statins lower serum LDL concentrations by upregulating the activity of LDL receptors and are responsible for clearing LDL from the blood. Some representative examples the statin compounds include rosuvastatin, pravastatin and its sodium salt, simvastatin, lovastatin, atorvastatin, fluvastatin, cerivastatin, rosuvastatin, pitavastatin, BMS's "superstatin", and HMG-CoA reductase inhibitors known in the art.

Suitable pharmaceutical agents that can be used in conjunction with compounds of the present invention include the angiotensin converting enzyme (ACE) inhibitors. The angiotensin converting enzyme inhibitors belong to the class of drugs that partially lower blood glucose levels as well as lowering blood pressure by inhibiting angiotensin converting enzymes. Examples of the angiotensin converting enzyme inhibitors include captopril, enalapril, alacepril, delapril; ramipril, lisinopril, imidapril, benazepril, ceronapril, cilazapril, enalaprilat, fosinopril, moveltopril, perindopril, quinapril, spirapril, temocapril, trandolapril, and angiotensin converting enzyme inhibitors known in the art.

Suitable pharmaceutical agents that can be used in conjunction with compounds of the present invention include the angiotensin II receptor antagonists. Angiotensin II receptor antagonists target the angiotensin II receptor subtype 1 (i.e., AT1) and demonstrate a beneficial effect on hypertension.

Examples of angiotensin II receptor antagonists include losartan (and the potassium salt form), and angiotensin II receptor antagonists known in the art.

Other treatments for one or more of the diseases cited herein include the use of pharmaceutical agents known in the art belonging to the classes of drugs referred to, but not limited to, the following: amylin agonists (for example, pramlintide), insulin secretagogues (for example, GLP-1 agonists; exendin-4; insulinotropin (NN2211); dipeptyl peptidase inhibitors (for example, NVP-DPP-728), acyl CoA cholesterol acetyltransferase inhibitors (for example, Ezetimibe, eflucimibe, and like compounds), cholesterol absorption inhibitors (for example, ezetimibe, pamaqueside and like compounds), cholesterol ester transfer protein inhibitors (for example, CP-529414, JTT-705, CETi-1, and like compounds), microsomal triglyceride transfer protein inhibitors (for example, implitapide, and like compounds), cholesterol modulators (for example, NO-1886, and like compounds), bile acid modulators (for example, GT103-279 and like compounds) and squalene synthase inhibitors.

Squalene synthesis inhibitors belong to a class of drugs that lower blood cholesterol levels by inhibiting synthesis of squalene. Examples of the squalene synthesis inhibitors include (S)-α-[Bis[2,2-dimethyl-1-oxopropoxy)methoxy] phosphinyl]-3-phenoxybenzenebutanesulfonic acid, mono potassium salt (BMS-188494) and squalene synthesis inhibitors known in the art.

Compositions of the Present Invention

According to a further aspect, the present invention also pertains to pharmaceutical compositions comprising one or more compounds of Formula (I) or any formulae disclosed herein, and one or more pharmaceutically acceptable carriers.

Some embodiments of the present invention include a method of producing a pharmaceutical composition comprising admixing at least one compound according to any of the compound embodiments disclosed herein and a pharmaceutically acceptable carrier.

Formulations may be prepared by any suitable method, typically by uniformly mixing the active compound(s) with liquids or finely divided solid carriers, or both, in the required proportions, and then, if necessary, forming the resulting mixture into a desired shape.

Conventional excipients, such as binding agents, fillers, acceptable wetting agents, tabletting lubricants, and disintegrants may be used in tablets and capsules for oral administration. Liquid preparations for oral administration may be in the form of solutions, emulsions, aqueous or oily suspensions, and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives, and flavorings and colorants may be added to the liquid preparations. Parenteral dosage forms may be prepared by dissolving the compound of the invention in a suitable liquid vehicle and filter sterilizing the solution before filling and sealing an appropriate vial or ampoule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, The Science and Practice of Pharmacy, 20$^{th}$ Edition, 2000, Lippincott Williams & Wilkins, (Editors: Gennaro, A. R., et al.).

While it is possible that, for use in the prophylaxis or treatment, a compound of the invention may, in an alternative use, be administered as a raw or pure chemical, it is preferable however to present the compound or active ingredient as a pharmaceutical formulation or composition further comprising a pharmaceutically acceptable carrier.

The invention thus further provides pharmaceutical formulations comprising a compound of the invention or a pharmaceutically acceptable salt or derivative thereof together with one or more pharmaceutically acceptable carriers thereof and/or prophylactic ingredients. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof, and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a solvate or physiologically functional derivative thereof can be used as active ingredients in pharmaceutical compositions, specifically as 5HT$_{2C}$ receptor agonists. By the term "active ingredient" is defined in the context of a "pharmaceutical composition" and shall mean a component of a pharmaceutical composition that provides the primary pharmacological effect, as opposed to an "inactive ingredient" which would generally be recognized as providing no pharmaceutical benefit.

The dose when using the compounds of the present invention can vary within wide limits, and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds of the present invention. Representative doses of the present invention include, but not limited to, about 0.001 mg to about 5000 mg, about 0.001 to about 2500 mg, about 0.001 to about 1000 mg, 0.001 to about 500 mg, 0.001 mg to about 250 mg, about 0.001 mg to 100 mg, about 0.001 mg to about 50 mg, and about 0.001 mg to about 25 mg. Multiple doses may be administered during the day, especially when relatively large amounts are deemed to be needed, for example 2, 3 or 4, doses. Depending on the individual and as deemed appropriate from the patient's physician or care-giver it may be necessary to deviate upward or downward from the doses described herein.

The amount of active ingredient, active salt or hydrate thereof, required for use in treatment will vary not only with the particular salt selected but also with the route of administration, the nature of the condition being treated and the age and condition of the patient and will ultimately be at the discretion of the attendant physician or clinician.

In general, one skilled in the art understands how to extrapolate in vivo data obtained in a model system, typically an animal model, to another, such as a human. Typically, animal models include, but are not limited to, rodent models. In some circumstances, these extrapolations may merely be based on the weight of the animal model in comparison to another, such as a mammal, preferably a human, however, more often, these extrapolations are not simply based on weights, but rather incorporate a variety of factors. Representative factors include, but are not limited to, the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds of the Formula (I) as part of combination-therapy. The dosage regimen for treating a disease condition with the compounds and/or compositions of the present invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4, part administrations. If appropriate, depending on individual behavior, it may be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, prefilled syringes, small volume infusion or in multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the Formula (I) or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the Formula (I) as an aerosol can be prepared by processes well-known to the person skilled in the art. For their preparation, for example, solutions or dispersions of the compounds of the Formula (I) in water, water/alcohol mixtures or suitable saline solutions can be employed using customary additives, for example benzyl alcohol or other suitable preservatives, absorption enhancers for increasing the bioavailability, solubilizers, dispersants and others, and, if appropriate, customary propellants, for example include carbon dioxide, CFC's, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfiric, tartaric, oxalic, p-toluenesulfonic and the like, such as those pharmaceutically acceptable salts listed in Journal of Pharmaceutical Science, 66, 2 (1977); incorporated herein by reference in its entirety.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the invention containing one or more specialized non-toxic protective groups used in a transient manner to alter or to eliminate a property of the compound. In general, the "pro-drug" approach is utilized to facilitate oral absorption. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference in their entirety.

Some embodiments of the present invention include a method of producing a pharmaceutical composition for "combination-therapy" comprising admixing at least one compound according to any of the compound embodiments disclosed herein, at least one pharmaceutical agent as described herein and a pharmaceutically acceptable carrier.

In some embodiments the pharmaceutical agents is selected from the group consisting of: apolipoprotein-B secretion/microsomal triglyceride transfer protein (apo-B/MTP) inhibitors, MCR-4 agonists, cholescystokinin-A (CCK-A) agonists, serotonin and norepinephrine reuptake inhibitors (for example, sibutramine), sympathomimetic agensts, $\beta_3$ adrenergic receptor agonists, dopamine agonists (for example, bromocriptine), melanocyte-stimulating hormone receptor analogs, cannabinoid 1 receptor antagonists [for example, SR141716: N-(piperidin-1-yl)-5-(4-chlorophenyl)-1-(2,4-dichlorophenyl)-4-methyl-1H-pyrazole-3-carboxamide], melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™), human agouti-related proteins (AGRP), ghrelin receptor antagonists, histamine 3 receptor antagonists or reverse agonists, neuromedin U receptor agonists, noradrenergic anorectic agents (for example, phentermine, mazindol and the like) and appetite suppressants (for example, bupropion). In further embodiments, the pharmaceutical agent is selected from the group consisting of orlistat, sibutramine, bromocriptine, ephedrine, leptin, and pseudoephedrine.

In some embodiments the pharmaceutical agents is selected from the group consisting of: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin II receptor antagonists and adiponectin.

It is noted that when the $5HT_{2C}$ receptor agonists are utilized as active ingredients in a pharmaceutical composition, these are not intended for use only in humans, but in other non-human mammals as well. Indeed, recent advances in the area of animal health-care mandate that consideration be given for the use of $5HT_{2C}$ receptor agonists for the treatment of obesity in domestic animals (e.g., cats and dogs), and $5HT_{2C}$ receptor agonists in other domestic animals where no disease or disorder is evident (e.g., food-oriented animals such as cows, chickens, fish, etc.). Those of ordinary skill in the art are readily credited with understanding the utility of such compounds in such settings.

Preparation of Compounds of the Invention

In the illustrated syntheses outlined below, the labeled substituents have the same identifications as set out in the definitions of the compounds of the present invention of Formula (I) and the Formulae of the subgenera as described herein.

Those of skill in the art will appreciate the wide variety of compounds of the present invention can be prepared according to Schemes I through V, Infra. One representative synthesis is set forth below in Scheme I, for when $R_2$ is methyl:

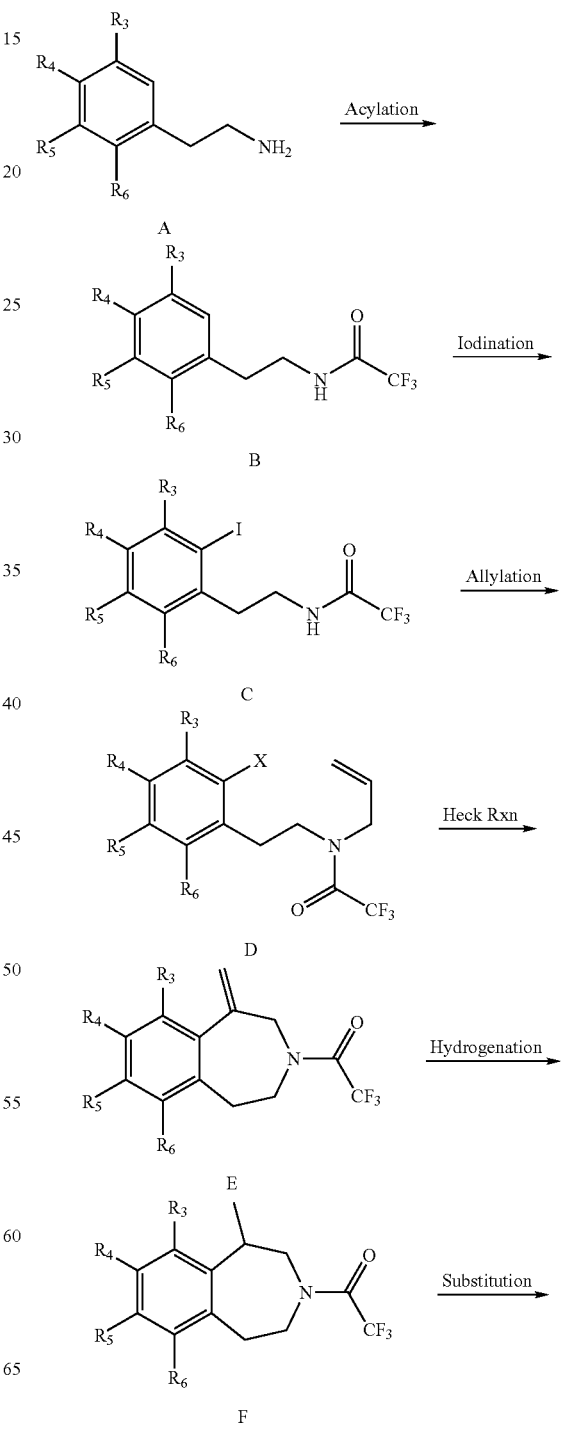

-continued

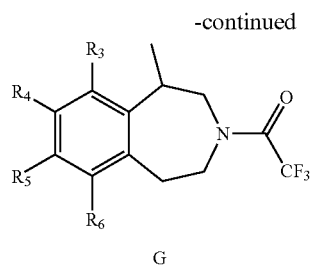

G

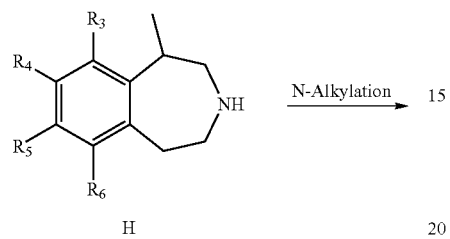

H

Scheme II

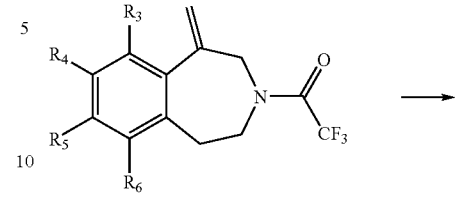

E

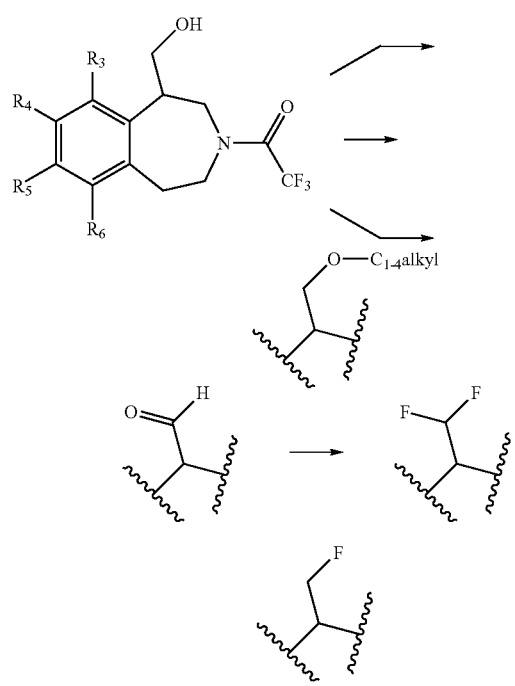

By utilizing, for example, an appropriately substituted 2-phenyl ethylamino Compound A having any of a wide variety of substituents $R_3$, $R_4$, $R_5$ and $R_6$ the corresponding substituted 1-methyl-2,3,4,5-tetrahydro-1H-3-benzazepine (Compound H can be prepared. In a subsequent step, Compound H can be readily alkylated by, for example, treatment with excess formaldehyde or formaldehyde equivalent such as paraformaldehyde (for methylation) or a higher order aldehyde, followed by reduction with $NaBH_3CN$ or similar reducing agent according to methodologies known in the art.

In addition, numerous synthetic transformations can be performed at different stages in the pathway illustrated in Scheme I to prepare additional compounds of Formula (I). For example, Compound E can be converted into a number of compounds of the invention including, $R_2$=—$CH_2OH$. In this case, the double bond of Compound E can be hydroborated using methods known in the art, such as diborane, disiamylborane and the like, to give a primary alcohol after oxidative workup (i.e., $H_2O_2$). Either the N-protection can be removed to give desired compounds of the invention or the primary alcohol can be subsequently converted to an ether using methods known in the art such as, for example, the Williamson ether procedure, using an alkyl halide in the presence of a base. In this example, the N-protection can be removed to give compounds of Formula (I) wherein $R_2$ is the group $CH_2O$—$C_{1-4}$ alkyl. Alternatively, the primary alcohol can be fluorinated using reagents known in the art, such as dialkylaminosulfur trifluorides and the like. Certain dialkylaminosulfur trifluorides include, but not limited to, bis(2-methoxyethyl)amino-sulfur trifluoride, (diethylamino)sulfur trifluoride, (dimethylamino)sulfur trifluoride, morpholinosulfur trifluoride and the like. Treatment with a fluorinating agent can give monofluoroalkyl compounds of Formula (I), wherein $R_2$ is —$CH_2F$. In addition, the primary alcohol prepared from Compound E can be further oxidized to give the corresponding aldehyde and in a similar manner subsequently converted to difluoroalkyl compounds of Formula (I), wherein $R_2$ is —$CHF_2$.

Reaction Scheme II is provided below showing these illustrative transformations and is not intended to be limiting:

Another representative synthetic pathway for the preparation of compounds of Formula (I) is set forth below in Reaction Scheme III:

Scheme III:

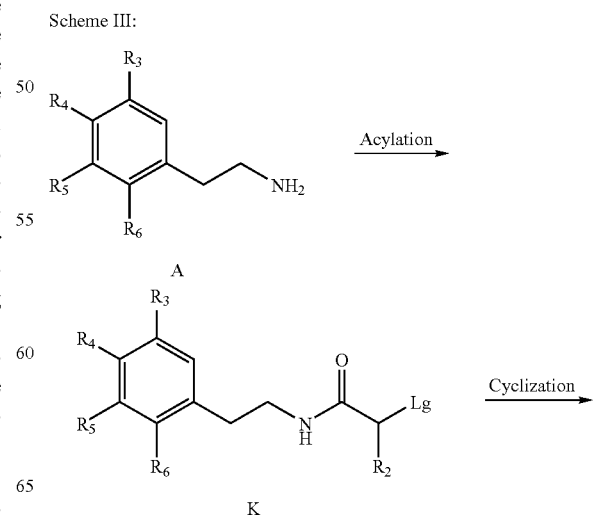

K

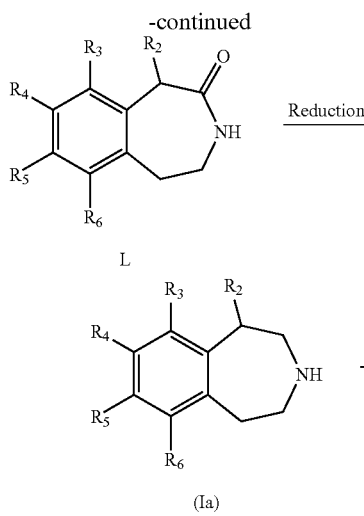

By utilizing, for example, an appropriately substituted 2-phenyl ethylamino Compound A having any of a wide variety of substituents $R_3$, $R_4$, $R_5$ and $R_6$ the corresponding 1-substituted-2,3,4,5-tetrahydro-1H-3-benzazepine [i.e., a compound of Formula (Ia)] can be prepared. Scheme III illustrates one general pathway for the introduction of $R_2$ groups into the compounds of the present invention. Compound A is acylated with a carboxylic acid derivative using one of the many methods, such as one of the commonly known coupling agents, available to the artisan. A particularly useful method uses an acid chloride as described in the Examples, Infra. The carboxylic acid derivative is selected to possess a leaving group or a moiety that can be converted into a leaving group (i.e., Lg). The resulting Compound K is cyclized in the presence of a Lewis Acid, such as, for example, aluminum chloride. After reduction, compounds of the invention are obtained wherein $R_1$ is H [i.e., a compound of Formula (Ia)].

One alternate synthetic approach that can be used to prepare compounds of the present invention utilizes Compound L (i.e., $R_2$ is H). In this method, the amide nitrogen is first alkylated (providing the $R_1$ group, Compound N) or protected (i.e., Compound O) using any number of the methods known in the art. The $R_2$ group is subsequently introduced via an alkylation reaction to provide Compounds P and Q respectively. Alkylation reactions can be conducted under basic conditions, for example, using DMF/NaH, and an alkylating agent of the formula $R_2$-Lg (wherein: $R_2$ has the same meaning as described herein and Lg is a leaving group known in the art, such as, Cl, Br, I, OMs, OTs and the like). Examples of the alkylating agent include, but are not limited to, $CH_3I$, $CH_3OMs$, $CH_3OTs$, $CH_3CH_2I$, $CF_3CH_2I$, $CF_3I$, $CH_3OCH_2Cl$ and the like. A representative alkylation example has been reported by Orito, K. and Matsuzaki, T. in Tetrahedron, 1980, 36, 81, 1017-1021 and is incorporated herein by reference in its entirety. In the example when the nitrogen is protected (i.e., Compound Q), the protecting group is first removed and the amide reduced to provide compounds of the invention wherein $R_1$ is H. In the example where the nitrogen is alkylated (i.e., Compound P), then the amide is merely reduced to provide compounds wherein $R_1$ is alkyl. This method is illustrated in Schemes IV and V below:

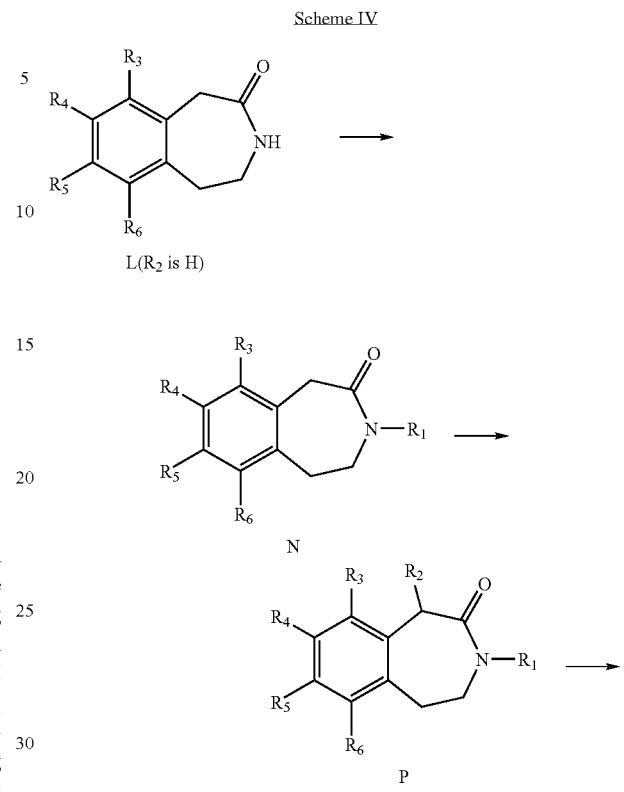

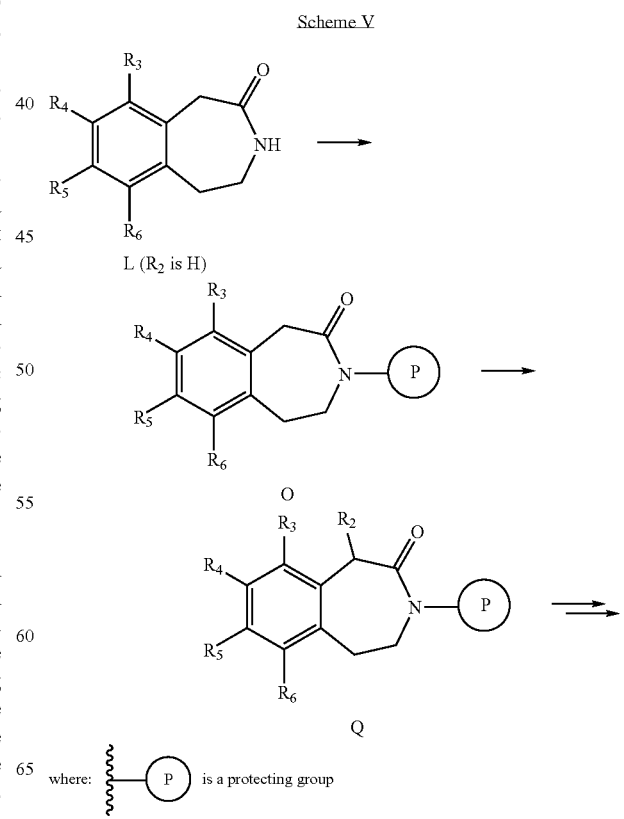

Those of skill in the art will appreciate that a wide variety of compounds of the present invention can be prepared according to Schemes I through V.

Protecting groups may be required for various functionality or functionalities during the synthesis of some of the compounds of the invention. Accordingly, representative protecting groups that are suitable for a wide variety of synthetic transformations are disclosed in Greene and Wuts, *Protective Groups in Organic Synthesis,* 3rd edition, John Wiley & Sons, New York, 1999, the disclosure of which is incorporated herein by reference in its entirety.

As described herein, compounds of the present invention can exist in various forms, for example, enantiomers and racemates. In is understood that the optically active forms can be obtained by resolution of the racemates, separated by chiral chromatography or by asymmetric synthesis using methods known in the art to obtain enantiomers.

Other Utilities

Another object of the present invention relates to radio-labeled compounds of Formula (I) that would be useful not only in radio-imaging but also in assays, both in vitro and in vivo, for localizing and quantitating the $5HT_{2C}$ receptor in tissue samples, including human, and for identifying $5HT_{2C}$ receptor ligands by inhibition binding of a radio-labeled compound. It is a further object of this invention to develop novel $5HT_{2C}$ receptor assays of which comprise such radio-labeled compounds.

The present invention embraces isotopically-labeled compounds of Formula (I) and any subgenera herein, such as but not limited to, Formula (Ia) through Formula (Is). An "isotopically" or "radio-labeled" compounds are those which are identical to compounds disclosed herein, but for the fact that one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro $5HT_{2C}$ receptor labeling and competition assays, compounds that incorporate $^3H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound of Formula (I) that has incorporated at least one radionuclide; in some embodiments the radionuclide is selected from the group consisting of $^3H$, $^{14}C$, $^{125}I$, $^{35}S$ and $^{82}Br$.

Certain isotopically-labeled compounds of the present invention are useful in compound and/or substrate tissue distribution assays. In some embodiments the radionuclide $^3H$ and/or $^{14}C$ isotopes are useful in these studies. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Schemes supra and Examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or the more scarce radio-isotope or nonradio-active isotope.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas—This procedure normally yields high specific activity products and requires halogenated or unsaturated precursors.

B. Reduction with Sodium Borohydride [$^3H$]—This procedure is rather inexpensive and requires precursors containing reducible functional groups such as aldehydes, ketones, lactones, esters, and the like.

C. Reduction with Lithium Aluminum Hydride [$^3H$]—This procedure offers products at almost theoretical specific activities. It also requires precursors containing reducible functional groups such as aldehydes, ketones, lactones, esters, and the like.

D. Tritium Gas Exposure Labeling—This procedure involves exposing precursors containing exchangeable protons to tritium gas in the presence of a suitable catalyst.

E. N-Methylation using Methyl Iodide [$^3H$]—This procedure is usually employed to prepare O-methyl or N-methyl ($^3H$) products by treating appropriate precursors with high specific activity methyl iodide ($^3H$). This method in general allows for higher specific activity, such as for example, about 70-90 Ci/mmol.

Synthetic methods for incorporating activity levels of $^{125}I$ into target molecules include:

A. Sandmeyer and like reactions—This procedure transforms an aryl or heteroaryl amine into a diazonium salt, such as a tetrafluoroborate salt, and subsequently to $^{125}I$ labeled compound using Na$^{125}I$. A represented procedure was reported by Zhu, D.-G. and co-workers in *J. Org. Chem.* 2002, 67, 943-948.

B. Ortho $^{125}$Iodination of phenols—This procedure allows for the incorporation of $^{125}I$ at the ortho position of a phenol as reported by Collier, T. L. and co-workers in *J. Labeled Compd Radiopharm.* 1999, 42, S264-S266.

C. Aryl and heteroaryl bromide exchange with $^{125}I$—This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A represented procedure was reported by Bas, M.-D. and co-workers in *J. Labeled Compd Radiopharm.* 2001, 44, S280-S282.

A radio-labeled $5HT_{2C}$ receptor compound of Formula (I) can be used in a screening assay to identify/evaluate compounds. In general terms, a newly synthesized or identified compound (i.e., test compound) can be evaluated for its ability to reduce binding of the "radio-labeled compound of Formula (I)" to the $5HT_{2C}$ receptor. Accordingly, the ability of a test compound to compete with the "radio-labeled compound of Formula (I)" for the binding to the $5HT_{2C}$ receptor directly correlates to its binding affinity.

The labeled compounds of the present invention bind to the $5HT_{2C}$ receptor. In one embodiment the labeled compound has an IC$_{50}$ less than about 500 µM, in another embodiment the labeled compound has an IC$_{50}$ less than about 100 µM, in yet another embodiment the labeled compound has an IC$_{50}$ less than about 10 µM, in yet another embodiment the labeled compound has an $IC_{50}$ less than about 1 μM, and in still yet another embodiment the labeled inhibitor has an $IC_{50}$ less than about 0.1 μM.

Other uses of the disclosed receptors and methods will become apparent to those in the art based upon, inter alia, a review of this disclosure.

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative and not intended to be limiting.

EXAMPLES

Example 1

Intracellular $IP_3$ Accumulation Assay:

HEK293 cells were transfected in 15 cm sterile dishes with or without (control) 16 ug of human $5HT_{2C}$ receptor cDNA [for example see, Saltzman, A. G., et al. *Biochem. Biophys. Res. Commun.* 181, 1469-1478 (1991)] using 25 ul of lipofectamine. Cells were then incubated for 3-4 hours at 37° C./5% $CO_2$ and then transfection media was removed and replaced with 100 ul of DMEM. Cells were then plated onto 100 cm sterile dishes. The next day cells were plated into 96 well PDL microtiter plates at a density of 55 K/0.2 ml. Six hours later, media was exchanged with [$^3$H]inositol (0.25 uCi/well) in inositol free DMEM and plates were incubated at 37° C./5% $CO_2$ overnight. The next day, wells were aspirated and 200 ul of DMEM containing test compound, 10 uM pargyline, and 10 mM LiCl was added to appropriate wells. Plates were then incubated at 37° C./5% $CO_2$ for three hours followed aspiration and by addition of fresh ice cold stop solution (1M KOH, 19 mM Na-borate, 3.8 mM EDTA) to each well. Plates were kept on ice for 5-10 min and the wells were neutralized by addition of 200 ul of fresh ice cold neutralization solution (7.5% HCl). Plates were then frozen until further processing is desired. The lysate was then transferred into 1.5 ml Eppendorf tubes and 1 ml of chloroform/methanol (1:2) was added/tube. The solution was vortexed for 15 seconds and the upper phase was applied to a Biorad AG1-X8™ anion exchange resin (100-200 mesh). First, the resin was washed with water at 1:1.25 W/V and 0.9 ml of upper phase was loaded onto the column. The column was then washed with 10 ml of 5 mM myo-inositol and 10 ml of 5 mM Na-borate/60 mM Na-formate. The inositol tris phosphates were eluted into scintillation vials containing 10 ml of scintillation cocktail with 2 ml of 0.1 M formic acid/1 M ammonium formate. The columns were regenerated by washing with 10 ml of 0.1 M formic acid/3M ammonium formate and rinsed twice with dd $H_2O$ and stored at 4° C. in water.

The biological activities in the IP Accumulation Assay for several representative compounds are shown in Table 3 below:

TABLE 3

| Compound No. | $5HT_{2C}$ ($IC_{50}$) IP Accumulation Assay (nM) |
|---|---|
| 1 | 11.7 |
| 3 | 24.5 |

The majority of the compounds of the Examples showed activities in the IP Accumulation Assay in the range between about 11 nM and about 5 μM.

Example 2

Inhibition of Food Intake in Food-deprived Rats

Male Sprague-Dawley rats (250-350 g) are deprived of food overnight prior to testing. Prior to food deprivation, the animals are weighed and separated into treatment groups in order to balance groups according to body weight. On the test day, animals are placed into individual cages (no bedding) at 9:00 am with free access to water. At 10:00 am, animals are injected with test compound (p.o., i.p., or s.c.) and then presented with a pre-weighed amount of food in a dish either 60 min (p.o.) or 30 min (i.p. and s.c.) after drug administration. Food consumption over different time points is determined by weighing the food cup at 1, 2, 4, and 6 hr after the food is presented. Thus, food consumption is measured at 2, 3, 5, and 7 hr post-injection in p.o. studies, and at 1.5; 2.5, 4.5, and 6.5 hr post-injection in i.p. and s.c. studies.

Example 3

Syntheses of Selected Compounds of the Invention

Example 3.1

Preparation of (R,S) 6,8-Dichloro-1-methyl-2,3,4,5-tetrahydro-1H-3-benzazepine (Also referred to herein as Compound 1)

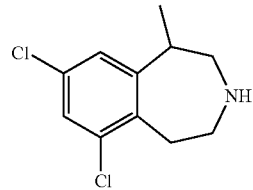

Step 1: Preparation of 2-chloro-N-[2-(2,4-dichlorophenyl) ethyl]propionamide.

A solution of 2,4-dichlorophenethylamine (1.0 g, 5.3 mmol) in dichloromethane (20 mL) was treated with diisopropylethylamine (0.82 g, 6.3 mmol) and 2-chloropropionylchloride (0.67 mL, 5.3 mmol) sequentially, and stirred at 20° C. for 4 hours. The mixture was diluted with dichloromethane (50 mL), washed with 10% aqueous HCl, brine (20 mL), dried with $Na_2SO_4$ and concentrated, resulting in 1.5 g of the desired product as a brown oil. MS calculated for $C_{11}H_{12}Cl_3NO+H$: 280, observed: 280.

Step 2: Preparation of 6,8-dichloro-1-methyl-2-oxo-2,3,5-trihydro-1H-3-benzazepine.

Neat 2-Chloro-N-[2-(2,4-dichlorophenyl)ethyl]propionamide (2.5 g, 9.1 mmol) and $AlCl_3$ (3.6 g, 27 mmol) were heated at 150° C. for 18 hours while stirring. The product mixture was quenched with water (10 mL), diluted with dichloromethane (100 mL), the organic phase separated, washed with brine (50 mL), dried with $Na_2SO_4$ and concentrated, resulting in 1.9 g of a brown oil. MS calculated for $C_{11}H_{11}Cl_2NO+H$: 244, observed: 244.

Step 3: Preparation of 6,8-dichloro-1-methyl-2,3,4,5-tetrahydro-1H-3-benzazepine.

A solution of 6,8-Dichloro-1-methyl-2-oxo-2,3,5-trihydro-1H-3-benzazepine (1.9 g, 7.8 mmol) in tetrahydrofuran (50 mL) was treated with 1.0 M borane in THF (20.0 mL, 20.0 mmol), and stirred at 20° C. for 5 hours. The mixture was quenched with methanol (10 mL), acidified with concentrated HCl (0.2 mL), azeotroped with methanol (3×100 mL) and concentrated. Flash chromatography (5% methanol in dichloromethane) resulted in 1.0 g of a clear oil. $^1$H NMR (400 MHz, CDCl$_3$) δ 7.20 (s, 1H), 6.90 (s, 1H), 4.30 (bs, 1H), 3.92 (m, 1H), 3.51 (m, 1H), 3.37 (m, 2H), 3.03 (m, 1H), 2.77 (m, 2H), 1.31 (d, J=8 Hz, 3H). MS calculated for C$_{11}$H$_{13}$Cl$_2$N+H: 230, observed: 230.

Example 3.2

Preparation of (R,S) 6-Chloro-1-methyl-2,3,4,5-tetrahydro-1H-3-benzazepine (Compound 2)

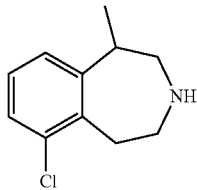

Compound 2 was prepared utilizing a similar procedure as described for the preparation of Compound 1. (R,S) 6-chloro-1-methyl-2,3,4,5-tetrahydro-1H-3-benzazepine was obtained from 2-chlorophenethylamine as a colorless oil. $^1$H NMR (400 MHz, CDCl$_3$) δ 7.17 (d, J=8 Hz, 1H), 6.93 (m, 2H), 3.97 (bs, 1H), 3.79 (m, 1H), 3.3-3.1 (m, 3H), 2.95 (d, J=11 Hz, 1H), 2.8-2.6 (m, 2H), 1.3 (d, J=8 Hz, 3H). MS calculated for C$_{11}$H$_{14}$ClN+H: 196, observed: 196.

Example 3.3

Preparation of (R,S) 8-Chloro-9-fluoro-1-methyl-2,3,4,5-tetrahydro-1H-3-benzazepine (Compound 3)

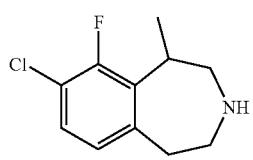

Step 1: Preparation of N-Trifluoroacetyl-8-chloro-9-fluoro-1-methyl-2,3,4,5-tetrahydro-1H-3-benzazepine.

A solution of N-trifluoroacetyl-8-chloro-1-methyl-2,3,4,5-tetrahydro-1H-3-benzazepine (2.5 g, 8.5 mmol) in 1,2-dichloroethane (15 mL) was treated with Selectfluor (3.9 g, 11 mmol), trifluoromethanesulfonic acid (8 mL, 90 mmol) and stirred 60 hours at 75° C. The product mixture was poured into water (200 mL), extracted with EtOAc (200 mL), the organic phase washed with saturated aqueous NaHCO$_3$ (2×100 mL), brine (100 mL), dried with Na$_2$SO$_4$ and concentrated. The crude product was purified by flash chromatography (6% EtOAc in hexane, silica) resulting in 0.6 g of a white solid. MS calculated for C$_{13}$H$_{12}$ClF$_4$NO+H: 310, observed: 310.

Step 2: Preparation of 8-Chloro-9-fluoro-1-methyl-2,3,4,5-tetrahydro-1H-3-benzazepine.

A solution of N-trifluoroacetyl-8-chloro-9-fluoro-1-methyl-2,3,4,5-tetrahydro-1H-3-benzazepine (160 mg, 0.22 mmol) in methanol (3 mL) was treated with 15% aqueous NaOH (2 mL), and stirred for 3.5 hours at 25° C. The product mixture was concentrated, extracted 3 times with CH$_2$Cl$_2$ (5 mL), dried with Na$_2$SO$_4$ and concentrated to give 93 mg of a clear oil. $^1$H NMR (400 MHz, CDCl$_3$) δ 7.06 (dd, J=8, 8 Hz, 1H), 6.75 (d, J=8 Hz, 1H), 3.58 (m, 1H), 3.25-3.15 (m, 3H), 2.93 (d, J=13 Hz, 1H) 2.75-2.60 (m, 3H), 1.96 (bs, 1H), 1.33 (d, J=8 Hz, 3H). MS calculated for C$_{11}$H$_{13}$ClFN+H: 214, observed: 214.

Example 3.4

Preparation of (R,S) 8,9-Dichloro-1-methyl-2,3,4,5-tetrahydro-1H-3-benzazepine (Compound 4)

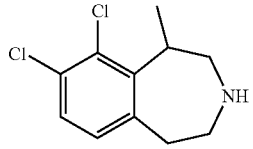

Compound 4 was prepared utilizing a similar procedure as described herein for the preparation of Compound 1. (R,S) 8,9-dichloro-1-methyl-2,3,4,5-tetrahydro-1H-3-benzazepine was obtained from 3,4-dichlorophenethylamine as a colorless oil. $^1$H NMR (400 MHz, CDCl$_3$) δ 7.40 (d, J=8 Hz, 1H), 7.16 (d, J=8 Hz, 1H), 4.17 (m, 1H), 3.55 (m, 2H), 3.5-3.3 (m, 2H), 3.2-3.0 (m, 2H), 1.43 (d, J=7 Hz, 3H). MS calculated for C$_{11}$H$_{13}$Cl$_2$N+H: 230, observed: 230.

Example 3.5

Preparation of (S)-8,9-dichloro-1-methyl-2,3,4,5-tetrahydro-1H-3-benzazepine (Compound 5)

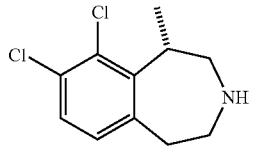

Step 1: Preparation of (S)-N-Trifluoroacetyl-8-chloro-1-methyl-2,3,4,5-tetrahydro-1H-3-benzazepine.

(S)-N-Trifluoroacetyl-8-chloro-1-methyl-2,3,4,5-tetrahydro-1H-3-benzazepine was prepared from (S)-8-chloro-1-methyl-2,3,4,5-tetrahydro-1H-3-benzazepine utilizing a similar procedure as described herein for the preparation of Compound 7 (one exception is that the resolution step was performed using D-tartaric acid). $^1$H NMR (400 MHz, CDCl$_3$, mixture of rotamers) δ 7.27 (m, 1H), 6.96 (m, 1H), 4.26 (bm, 0.6H), 4.19-4.03 (m, 1.7H), 3.92-3.87 (m, 0.8H) 3.75-3.69 (m, 0.8H), 3.47-3.22 (m, 2H), 2.91 (m, 1H), 1.28-1.25 (m, 3H). MS calculated for C$_{13}$H$_{13}$ClF$_3$NO+H: 292, observed: 292.

Step 2: Preparation of (S)-N-Trifluoroacetyl-8,9-dichloro-1-methyl-2,3,4,5-tetrahydro-1H-3-benzazepine.

A solution of (S)-N-Trifluoroacetyl-8-chloro-1-methyl-2,3,4,5-tetrahydro-1H-3-benzazepine (0.62 g, 2.1 mmol) in dichloromethane (10 mL) was treated with N-chlorosuccinimide (0.284 g, 2.1 mmol) and trifluoromethanesulfonic acid (0.639 g, 4.2 mmol). The reaction was stirred for 16 h at 20° C., diluted with water (20 mL) and extracted with dichloromethane (25 mL). The organics were dried with MgSO₄, filtered and concentrated. HPLC purification was done to provide 0.078 g of a white solid. ¹H NMR (400 MHz, CDCl₃, mixture of rotamers) δ 7.32-7.25 (m, 1H), 6.97-6.93 (m, 1H), 4.27-4.24 (m, 0.6H), 4.19-4.13 (m, 1H), 4.08-4.01 (m, 1H), 3.91-3.86 (0.8H, m), 3.74-3.69 (m, 0.8H:), 3.45-3.37 (m, 1H), 3.31-3.21 (m, 1H), 2.96-2.80 (m, 1H), 1.28-1.22 (m, 3H). MS calculated for $C_{13}H_{12}Cl_2F_3NO+H$: 326, observed: 326.

Step 3: Preparation of (S)-8,9-dichloro-1-methyl-2,3,4,5-tetrahydro-1H-3-benzazepine.

A solution of (S)-N-trifluoroacetyl-8,9-dichloro-1-methyl-2,3,4,5-tetrahydro-1H-3-benzazepine (0.270 g, 1.2 mmol) in methanol (10 mL) was treated with 15% aqueous NaOH (10 mL), and stirred for 3.5 hours at 25° C. The product mixture was concentrated, extracted 3 times with CH₂Cl₂ (25 mL), dried with Na₂SO₄ and concentrated to give 0.270 g of a clear oil. ¹H NMR (400 MHz, CDCl₃) δ 7.40 (d, J=8 Hz, 1H), 7.16 (d, J=8 Hz, 1H), 4.17 (m, 1H), 3.55 (m, 2H), 3.5-3.3 (m, 2H), 3.2-3.0 (m, 2H), 1.43 (d, J=7 Hz, 3H). MS calculated for $C_{11}H_{13}Cl_2N+H$: 230, observed: 230.

Example 3.6

Preparation of (S)-8-chloro-9-fluoro-1-methyl-2,3,4,5-tetrahydro-1H-3-benzazepine (Compound 6)

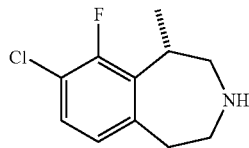

Step 1: Preparation of (S)-N-Trifluoroacetyl-8-chloro-9-fluoro-1-methyl-2,3,4,5-tetrahydro-1H-3-benzazepine.

A solution of (S)-N-trifluoroacetyl-8-chloro-1-methyl-2,3,4,5-tetrahydro-1H-3-benzazepine (2.5 g, 8.5 mmol) in 1,2-dichloroethane (15 mL) was treated with Selectfluor (3.9 g, 11 mmol), trifluoromethanesulfonic acid (8 mL, 90 mmol) and stirred 60 hours at 75° C. The product mixture was poured into water (200 mL), extracted with EtOAc (200 mL), the organic phase washed with saturated aqueous NaHCO₃ (2×100 mL), brine (100 mL), dried with Na₂SO₄ and concentrated. The crude product was purified by flash chromatography (6% EtOAc in hexane, silica) resulting in 0.6 g of a white solid. MS calculated for $C_{13}H_{12}ClF_4NO+H$: 310, observed: 310.

Step 2: Preparation of (S)-8-chloro-9-fluoro-1-methyl-2,3,4,5-tetrahydro-1H-3-benzazepine.

A solution of (S)-N-trifluoroacetyl-8-chloro-9-fluoro-1-methyl-2,3,4,5-tetrahydro-1H-3-benzazepine (160 mg, 0.22 mmol) in methanol (3 mL) was treated with 15% aqueous NaOH (2 mL), and stirred for 3.5 hours at 25° C. The product mixture was concentrated, extracted 3 times with CH₂Cl₂ (5 mL), dried with Na₂SO₄ and concentrated to give 93 mg of a clear oil. ¹H NMR (400 MHz, CDCl₃) δ 7.06 (dd, J=8, 8 Hz, 1H), 6.75 (d, J=8 Hz, 1H), 3.58 (m, 1H), 3.25-3.15 (m, 3H), 2.93 (d, J=13 Hz, 1H) 2.75-2.60 (m, 3H), 1.96 (bs, 1H), 1.33 (d, J=8 Hz, 3H). MS calculated for $C_{11}H_{13}ClFN+H$: 214, observed: 214.

Example 3.7

Preparation of (R)-8,9-dichloro-1-methyl-2,3,4,5-tetrahydro-1H-3-benzazepine (Compound 7)

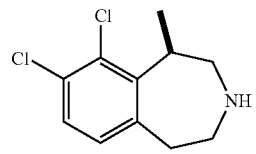

Step 1: Preparation of 2-(4-chlorophenyl)ethyl-N-2-chloropropionamide

To a 1-liter, 3-necked round bottom flask under argon balloon equipped with reflux condenser and addition funnel, were added sequentially 2-(4-chlorophenyl) ethylamine (30 g, 193 mmol), 400 mL acetonitrile, triethylamine (19.5 g, 193 mmol) and 80 mL acetonitrile. The clear colorless solution was stirred and cooled to 0° C. 2-Chloropropionyl chloride (24.5 g, 193 mmol, distilled) in 5 mL acetonitrile was slowly added over 20 minutes to evolution of white gas, formation of white precipitate, and color change of reaction mixture to slight yellow. An additional 10 mL of acetonitrile was used to rinse the addition fennel. The mixture was stirred at 0° C. for 30 minutes and then warmed to room temperature and stirred vigorously for an additional one hour. The yellow reaction mixture was concentrated on the rotary evaporator to a solid containing triethylamine hydrochloride (76.36 grams). This material was taken up in 100 mL ethylacetate and 200 mL water, and stirred vigorously. The layers were separated and the aqueous layer was extracted with an additional 100 mL ethylacetate. The combined organic layers were washed twice with 25 mL of saturated brine, dried over magnesium sulfate, filtered, and concentrated to a light tan solid (41.6 grams, 88%). TLC in ethylacetate-hexane, 8:2 showed a major spot two-thirds of the way up the plate and a small spot at the baseline. Baseline spot was removed as follows: This material was taken up in 40 mL of ethylacetate and hexane was added until the solution became cloudy. Cooling to 0° C. produced a white crystalline solid (40.2 grams, 85% yield). The product is a known compound (Hasan et al., *Indian J. Chem.*, 1971, 9(9), 1022) with CAS Registry No. 34164-14-2. LC/MS gave product 2.45 minute; 246.1 M⁺+H⁺. ¹H NMR (CDCl₃): δ 7.2 (dd, 4H, Ar), 6.7 (br S, 1H, NH), 4.38 (q, 1H, CHCH₃), 3.5 (q, 2H, ArCH₂CH₂NH), 2.8 (t, 2H, ArCH₂), 1.7 (d, 3H, CH₃). ¹³C NMR (CDCl₃): 169 (1C, C=O), 136 (1C, Ar—Cl), 132 (1C, Ar), 130 (2C, Ar), 128 (2C, Ar), 56 (1C, CHCl), 40 (1C, CHN), 34 (1C, CHAr), 22 (1C, CH₃).

Step2: Preparation of 8-chloro-1-methyl-2,3,4,5-tetrahydro-1H-3-benzazepin-2-one.

2-(4-Chlorophenyl)ethyl-N-2-chloropropionamide (10 g, 40.6 mmol) and aluminum chloride (16 g, 119.9 mmol) were added to a clean dry 100 mL round bottom flask equipped with an argon balloon, stirring apparatus, and heating apparatus. The white solid melted to a tan oil with bubbling at 91° C. (Note: if impure starting materials are used, a black tar can result but clean product can still be isolated). The mixture was heated and stirred at 150° C. for 12 hours. The reaction can be followed by LC/MS with the starting material at 2.45 minutes (246.1 M⁺+H⁺), the product at 2.24 minutes (209.6 M⁺+H⁺) on a 5 minute reaction time from 5-95% w/0.01% TFA in water/MeCN (50:50). After cooling to room temperature, the reaction mixture was quenched with slow addition of 10 mL of MeOH followed by 5 mL of 5% HCl in water and 5 mL of ethyl acetate. After separation of the resulting layers, the aqueous layer was extracted a second time with 10 mL of ethyl acetate. The combined organic layers were dried over magnesium sulfate, filtered, and concentrated to a tan solid (6.78 grams, 80% yield). LC/MS showed one peak, at 2.2 min and 209.6 MI. This material was taken up in ethyl acetate, filtered through celite and Kieselgel 60 (0.5 inch plug on a 60 mL Buchner funnel) and the filtrate was recrystallized from hexane/ethyl acetate to give final product (4.61 grams, 54% yield). $^1$H NMR (CDCl$_3$): δ 7.3-7.1 (m, 3H, Ar), 5.6 (br s, 1H, NH), 4.23 (q, 1H, CHCH$_3$), 3.8 (m, 1H, ArCH$_2$CH$_2$NH), 3.49 (m, 1H, ArCH$_2$CH$_2$NH), 3.48 (m, 1H, ArCH$_2$CH$_2$NH), 3.05 (m, 1H, ArCH$_2$CH$_2$NH), 1.6 (d, 3H, CH$_2$). $^{13}$C NMR (CDCl$_3$): 178 (1C, C=O), 139 (1C, Ar), 135 (1C, Ar), 130, 129 (2C, Ar), 126 (2C, Ar), 42 (1C, C), 40 (1C, CHN), 33 (1C, CHAr), 14 (1C, CH$_3$).

Step 3: Preparation of 8-chloro-1-methyl-2,3,4,5-tetrahydro-1H-3-benzazepine.

8-Chloro-1-methyl-2,3,4,5-tetrahydro-1H-3-benzazapin-2-one (150 mg, 0.716 mmol, purified by HPLC or recrystallization) was added to a 50 mL round bottom flask with 2M borane-tetrahydrofuran solution (2 mL, 2.15 mmol). The mixture was stirred 10 hours at room temperature under an argon balloon. LC/MS showed the desired product as the major peak with approximately 5% of starting material still present. The reaction mixture was quenched with 5 mL methanol and the solvents were removed on the rotary evaporator. This procedure was repeated with methanol addition and evaporation. The mixture was evaporated on the rotary evaporator followed by 2 hours in vacuo to give the product as a white solid (117 mg, 70 % yield). $^1$H NMR (CDCl$_3$): δ 10.2 (br s, 1H), 9.8 (br s, 1H), 7.14 (dd, 1H, J=2, 8 Hz), 7.11 (d, 1H, J=2 Hz), 7.03 (d, 1H, J=8 Hz), 3.6 (m, 2H), 3.5 (m, 2H), 2.8-3.0 (m, 3H), 1.5 (d, 3H, J=7 Hz). LC/MS: 1.41 minute, 196.1 M+H$^+$ and 139 major fragment.

Step 4: Preparation of L-(+)-tartaric acid salt of (R)-8-chloro-1-methyl-2,3,4,5-tetrahydro-1H-3-benzazepine.

To a clean, dry 50 mL round bottom flask were added 11.5 g (0.06 mol) of 8-chloro-1-methyl-2,3,4,5-tetrahydro-1H-3-benzazepine to 2.23 g (0.015 mol) of L-(+)-tartaric acid. The suspension was diluted with 56 g of tert-butanol and 6.5 mL of H$_2$O. The mixture was heated to reflux (75-78° C.) and stirred for 10 min to obtain a colorless solution. The solution was slowly cooled down to room temperature (during 1 h) and stirred for 3 h at room temperature. The suspension was filtered and the residue was washed twice with acetone (10 mL). The product was dried under reduced pressure (50 mbar) at 60° C. to yield 6.3 g of the tartrate salt (ee=80). This tartrate salt was added to 56 g of tert-butanol and 6.5 mL of H$_2$O. The resulting suspension was heated to reflux and 1 to 2 g of H$_2$O was added to obtain a colorless solution. The solution was slowly cooled down to room temperature (over the course of 1 h) and stirred for 3 h at room temperature. The suspension was filtered and the residue was washed twice with acetone (10 mL). The product was dried under reduced pressure (50 mbar) at 60° C. to produce 4.9 g (48% yield) of product (ee>98.9).

Step 5: Conversion of Salt to Free Amine—(R)-8-chloro-1-methyl-2,3,4,5-tetrahydro-1H-3-benzazepine.

The L-tartaric acid salt of 8-chloro-1-methyl-2,3,4,5-tetrahydro-1H-3-benzazepine (300 mg, 0.87 mmol) was added to a 25 mL round bottom flask with 50% sodium hydroxide solution (114 μL, 2.17 mmol) with an added 2 mL of water. The mixture was stirred 3 minutes at room temperature. The solution was extracted with methylene chloride (5 mL) twice. The combined organic extracts were washed with water (5 mL) and evaporated to dryness on the pump to afford free amine (220 mg crude weight). LC/MS 196 M+H).

Step 6: Preparation of (R)-N-Trifluoroacetyl-8-chloro-1-methyl-2,3,4,5-tetrahydro-1H-3-benzazepine.

A solution of (R)-8-chloro-1-methyl-2,3,4,5-tetrahydro-1H-3-benzazepine hydrochloride salt (1.0 g, 4.31 mmol) in dichloromethane (50 mL) at 0° C. was treated with pyridine (1.0 mL) and trifluoroacetic anhydride (1.35 g, 6.46 mmol). This was warmed to 20° C., stirred for 3 h and diluted with 1M HCl (25 mL). This was extracted with dichloromethane (2×50 mL) and the organics dried with MgSO$_4$, filtered and concentrated to give 1.17 g as an off-white solid. $^1$H NMR (400 MHz, CDCl$_3$, mixture of rotamers) δ 7.27 (m, 1H), 6.96 (m, 1H), 4.26 (bm, 0.6H), 4.19-4.03 (m, 1.7H), 3.92-3.87 (m, 0.8H), 3.75-3.69 (m, 0.8H), 3.47-3.22 (m, 2H), 2.91 (m, 1H), 1.28-1.25 (m, 3H). MS calculated for C$_{13}$H$_{13}$ClF$_3$NO+H: 292, observed: 292.

Step 7: (R)-8,9-dichloro-1-methyl-2,3,4,5-tetrahydro-1H-3-benzazepine

Compound,7 was prepared from (R)-N-trifluoroacetyl-8-chloro-1-methyl-2,3,4,5-tetrahydro-1H-3-benzazepine utilizing a similar two step procedure as described herein for the preparation of Compound 5. $^1$H NMR (400 MHz, CDCl$_3$) δ 7:40 (d, J=8 Hz, 1H), 7.16 (d, J=8 Hz, 1H), 4.17 (m, 1H), 3.55 (m, 2H), 3.5-3.3 (m, 2H), 3.2-3.0 (m, 2H), 1.43 (d, J=7 Hz, 3H). MS calculated for C$_{11}$H$_{13}$Cl$_2$N+H: 230, observed: 230.

Example 3.8

Preparation of (S)-9-bromo-8-chloro-1-methyl-2,3,4,5-tetrahydro-1H-3-benzazepine (Compound 8)

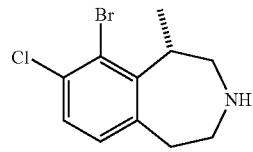

Step 1: Preparation of (S)-N-Trifluoroacetyl-9-bromo-8-chloro-1-methyl-2,3,4,5-tetrahydro-1H-3-benzazepine.

A solution of (S)-N-Trifluoroacetyl-8-chloro-1-methyl-2,3,4,5-tetrahydro-1H-3-benzazepine (0.875 g, 3.0 mmol) in dichloroethane (7 mL) was treated with N-bromosuccinimide (0.284 g, 2.1 mmol) and trifluoromethansulfonic acid (0.639 g, 4.2 mmol). The reaction was stirred for 16 h at 75° C., diluted with ethyl acetate (20 mL) and extracted with water (2×10 mL). The organics were dried with MgSO$_4$, filtered and concentrated. Flash chromatography (5% EtOAc in hexanes, silica) resulted in 0.13 g of a clear oil. MS calculated for C$_{13}$H$_{12}$BrClF$_3$NO+H: 370, observed: 370.

Step 2: Preparation of (S)-9-bromo-8-chloro-1-methyl-2,3,4,5-tetrahydro-1H-3-benzazepine.

Compound 8 was prepared from (S)-N-trifluoroacetyl-9-bromo-8-chloro-1-methyl-2,3,4,5-tetrahydro-1H-3-benzazepine utilizing a similar procedure as described herein for the preparation of Compound 5. (S)-9-bromo-8-chloro-1-methyl-2,3,4,5-tetrahydro-1H-3-benzazepine was obtained from (S)-N-trifluoroacetyl-9-bromo-8-chloro-1-methyl-2,3,4,5-tetrahydro-1H-3-benzazepine. $^1$H NMR (400 MHz, CDCl$_3$) δ 7.17 (d, J=8 Hz, 1H), 6.92 (d, J=8 Hz, 1H), 3.92-3.87 (m, 1H), 3.29-3.20 (m, 2H), 3.11 (dd, J=14, 5 Hz, 1H), 2.99 (dd, J=14, 2 Hz, 1H), 2.74-2.65 (m, 2H), 1.32 (d, J=7 Hz, 3H). MS calculated for $C_{11}H_{13}BrClN+H$: 274, observed: 274.

Example 3.9

Preparation of (R)-N-methyl-8,9-dichloro-1-methyl-2,3,4,5-tetrahydro-1H-3-benzazepine (Compound 9)

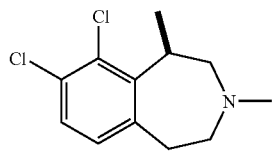

A solution of (R)-8,9-dichloro-1-methyl-2,3,4,5-tetrahydro-1H-3-benzazepine (0.05 g, 0.20 mmol) in dichloroethane (3 mL) was treated with sodium triacetoxyborohydride (0.073 g, 0.35 mmol) and formaldehyde (0.017 mL, 37% solution in water). This was stirred at 20° C. for 2 h. The reaction was diluted with 15% NaOH and extracted with ethyl acetate (2×10 mL). The organics were dried with $MgSO_4$, filtered and concentrated to give 0.042 g as an oil. $^1H$ NMR (400 MHz, $CDCl_3$) δ 7.19 (d, J=8 Hz, 1H), 6.89 (d, J=8 Hz, 1H), 3.91-3.88 (m, 1H), 3.28 (ddd, J=15, 12, 2 Hz, 1H), 2.99-2.88 (m, 2H), 2.68 (ddd, J=15, 5, 1 Hz, 1H), 2.36-2.32 (m, 4H), 2.13 (t, J=11 Hz, 1H), 1.27 (d, J=7 Hz, 3H). MS calculated for $C_{12}H_{15}Cl_2N+H$: 243, observed: 243.

Example 3.10

Preparation of (S)-N-methyl-8,9-dichloro-1-methyl-2,3,4,5-tetrahydro-1H-3-benzazepine (Compound 10)

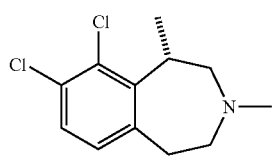

Step 1: Preparation of (S)-N-methyl-8,9-dichloro-1-methyl-2,3,4,5-tetrahydro-1H-3-benzazepine.

Compound 10 was prepared from (S)-8,9-dichloro-1-methyl-2,3,4,5-tetrahydro-1H-3-benzazepine utilizing a similar procedure as described herein for the preparation of Compound 9. $^1H$ NMR (400 MHz, $CDCl_3$) δ 7.19 (d, J=8 Hz, 1H), 6.89 (d, J=8 Hz, 1H), 3.91-3.88 (m, 1H), 3.28 (ddd, J=15, 12, 2 Hz, 1H), 2.99-2.88 (m, 2H), 2.68 (ddd, J=15, 5, 1 Hz, 1H), 2.36-2.32 (m, 4H), 2.13 (t, J=11 Hz, 1H), 1.27 (d, J=7 Hz, 3H). MS calculated for $C_{12}H_{15}Cl_2N+H$: 243, observed: 243.

Example 3.11

Preparation of (S)-N-methyl-9-bromo-8-chloro-1-methyl-2,3,4,5-tetrahydro-1H-3-benzazepine (Compound 11)

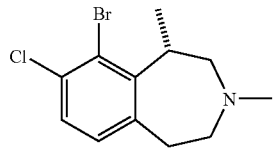

Compound 11 was prepared from (S)-9-bromo-8-chloro-1-methyl-2,3,4,5-tetrahydro-1H-3-benzazepine utilizing a similar procedure as described herein for the preparation of Compound 9. $^1H$ NMR (400 MHz, $CDCl_3$) δ 7.18 (d, J=8 Hz, 1H), 6.92 (d, J=8 Hz, 1H), 3.94-3.88 (m, 1H), 3.29 (ddd, J=15, 12, 2 Hz, 1H), 2.98-2.93 (m, 1H), 2.90 (ddd, J=15, 6, 1 Hz; 1H), 2.36-2.32 (m, 4H) 2.13 (t, J=11 Hz, 1H), 1.33 (d, J=7 Hz, 3H). MS calculated for $C_{12}H_{15}Cl_2N+H$: 288, observed: 288.

Example 4

Separation of Enantiomers for Selected Compounds of the Invention

Compounds of the present invention can be separated into their respective enantiomers using a Varian ProStar HPLC system with a 20 mm×250 mm Chiralcel OD chiral column, eluting with 0.2% diethylamine in various concentrations of isopropanol (IPA) in hexanes, for example, 5% IPA in hexanes, 1% IPA in hexanes and like concentrations.

It is intended that each of the patents, applications, printed publications, and other published documents mentioned or referred to in this specification be herein incorporated by reference in their entirety.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What we claim is:

1. A compound of Formula (I):

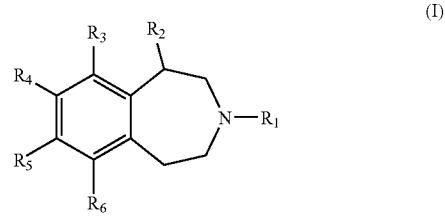

wherein:
R$_1$ is H or C$_{1-8}$ alkyl;
R$_2$ is C$_{1-4}$ alkyl, —CH$_2$—O—C$_{1-4}$ alkyl, C$_{1-4}$ haloalkyl or CH$_2$OH; and
R$_3$, R$_4$, R$_5$ and R$_6$ are each independently H, C$_{1-4}$ alkyl, amino, cyano, halogen, C$_{1-4}$ haloalkyl, nitro or OH; or a pharmaceutically acceptable salt thereof;
provided that when $R_2$ is $C_{1-4}$ alkyl, —$CH_2$—O—$C_{1-4}$ alkyl, or $CH_2OH$ then $R_3$ and $R_6$ are not both hydrogen.

2. The compound according to claim 1, or a pharmaceutically acceptable salt thereof, wherein $R_1$ is H.

3. The compound according to claim 1, or a pharmaceutically acceptable salt thereof, wherein $R_1$ is $C_{1-8}$ alkyl.

4. The compound according to claim 1, or a pharmaceutically acceptable salt thereof, wherein $R_2$ is $C_{1-4}$ alkyl.

5. The compound according to claim 1, or a pharmaceutically acceptable salt thereof, wherein $R_2$ is methyl.

6. The compound according to claim 1, or a pharmaceutically acceptable salt thereof, wherein $R_2$ is $C_{1-4}$ haloalkyl.

7. The compound according to claim 1, or a pharmaceutically acceptable salt thereof, wherein $R_3$ is H.

8. The compound according to claim 1, or a pharmaceutically acceptable salt thereof, wherein $R_3$ is $C_{1-4}$ alkyl.

9. The compound according to claim 1, or a pharmaceutically acceptable salt thereof, wherein $R_3$ is halogen.

10. The compound according to claim 1, or a pharmaceutically acceptable salt thereof, wherein $R_3$ is $C_{1-4}$ haloalkyl.

11. The compound according to claim 1, or a pharmaceutically acceptable salt thereof, wherein $R_4$ is H.

12. The compound according to claim 1, or a pharmaceutically acceptable salt thereof, wherein $R_4$ is $C_{1-4}$ alkyl.

13. The compound according to claim 1, or a pharmaceutically acceptable salt thereof, wherein $R_4$ is halogen.

14. The compound according to claim 1, or a pharmaceutically acceptable salt thereof, wherein $R_4$ is $C_{1-4}$ haloalkyl.

15. The compound according to claim 1, or a pharmaceutically acceptable salt thereof, wherein $R_5$ is H.

16. The compound according to claim 1, or a pharmaceutically acceptable salt thereof, wherein $R_5$ is $C_{1-4}$ alkyl.

17. The compound according to claim 1, or a pharmaceutically acceptable salt thereof, wherein $R_5$ is halogen.

18. The compound according to claim 1, or a pharmaceutically acceptable salt thereof, wherein $R_5$ is $C_{1-4}$ haloalkyl.

19. The compound according to claim 1, or a pharmaceutically acceptable salt thereof, wherein $R_6$ is H.

20. The compound according to claim 1, or a pharmaceutically acceptable salt thereof, wherein $R_6$ is $C_{1-4}$ alkyl.

21. The compound according to claim 1, or a pharmaceutically acceptable salt thereof, wherein $R_6$ is halogen.

22. The compound according to claim 1, or a pharmaceutically acceptable salt thereof, wherein $R_6$ is $C_{1-4}$ haloalkyl.

23. The compound of claim 1 selected from:
6,8-Dichloro-1-methyl-2,3,4,5-tetrahydro-1H-3-benzazepine;
6-Chloro-1-methyl-2,3,4,5-tetrahydro-1H-3-benzazepine;
8-Chloro-9-fluoro-1-methyl-2,3,4,5-tetrahydro-1H-3-benzazepine; and
8,9-Dichloro-1-methyl-2,3,4,5-tetrahydro-1H-3-benzazepine; or a pharmaceutically acceptable salt thereof.

24. The compound of claim 1 that is 9-bromo-8-chloro-1-methyl-2,3,4,5-tetrahydro-1H-3-benzazepine; or a pharmaceutically acceptable salt thereof.

25. The compound of claim 1 selected from:
N-methyl-8,9-dichloro-1-methyl-2,3,4,5-tetrahydro-1H-3-benzazepine; and
N-methyl-9-bromo-8-chloro-1-methyl-2,3,4,5-tetrahydro-1H-3-benzazepine; or a pharmaceutically acceptable salt thereof.

26. The compound according to claim 1, or a pharmaceutically acceptable salt thereof, wherein said compound is an R enantiomer.

27. The compound according to claim 1, or a pharmaceutically acceptable salt thereof, wherein said compound is an S enantiomer.

28. A pharmaceutical composition comprising a compound according to claim 1, or a pharmaceutically acceptable salt thereof, and a pharmaceutically acceptable carrier.

29. A method of treatment of a disorder selected from Male erectile dysfunction, and obesity, comprising administering to an individual in need of such treatment a therapeutically effective amount of a compound according to claim 1, or a pharmaceutically acceptable salt thereof.

30. The method according to claim 29 wherein the disorder is obesity.

31. The method according to claim 29 wherein the disorder is Male erectile dysfunction.

32. The method according to claim 30 or 31 wherein said individual is a human.

33. A method of decreasing food intake of an individual comprising administering to said individual a therapeutically effective amount of a compound according to claim 1, or a pharmaceutical acceptable salt thereof.

34. The method according to claim 33 wherein said individual is a human.

35. A method of inducing satiety in an individual comprising administering to said individual a therapeutically effective amount of a compound according to claim 1, or a pharmaceutical acceptable salt thereof.

36. The method according to claim 35 wherein said individual is a human.

37. A method of controlling weight gain of an individual comprising administering to said individual suffering from weight control a therapeutically effective amount of a compound according to claim 1, or a pharmaceutical acceptable salt thereof.

38. The method according to claim 37 wherein said individual is a human.

39. A method of producing a pharmaceutical composition comprising admixing at least one compound according to claim 1, or a pharmaceutically acceptable salt thereof, and a pharmaceutically acceptable carrier.

40. The compound according to claim 1, or a pharmaceuttically acceptable salt thereof, wherein:
$R_1$ is H, methyl, ethyl, n-propyl, iso-propyl or n-butyl;
$R_2$ is methyl, ethyl, iso-propyl, n-butyl or —$CF_3$;
$R_3$ is H, —$CH_3$, amino, cyano, fluorine atom, chlorine atom, bromine atom, iodine atom, $CF_3$, nitro or —OH;
$R_4$ is H, —$CH_3$, amino, cyano, fluorine atom, chlorine atom, bromine atom, iodine atom, $CF_3$, nitro or —OH;
$R_5$ is H, —$CH_3$, amino, cyano, fluorine atom, chlorine atom, bromine atom, iodine atom, $CF_3$, nitro or —OH; and
$R_6$ is H, —$CH_3$, amino, cyano, fluorine atom, chlorine atom, bromine atom, iodine atom, $CF_3$, nitro or —OH.

* * * * *

UNITED STATES PATENT AND TRADEMARK OFFICE
CERTIFICATE OF CORRECTION

| | | |
|---|---|---|
| PATENT NO. | : 7,704,993 B2 | Page 1 of 1 |
| APPLICATION NO. | : 10/561071 | |
| DATED | : April 27, 2010 | |
| INVENTOR(S) | : Brian Smith et al. | |

It is certified that error appears in the above-identified patent and that said Letters Patent is hereby corrected as shown below:

In the Specification

Col. 1, line 46, "perceHnt" should read -- percent --.

Col. 10, lines 9-31 should be single spaced.

Col. 23, line 9, "present can" should read -- present invention can --.

Signed and Sealed this

Seventh Day of December, 2010

David J. Kappos
*Director of the United States Patent and Trademark Office*